US012753176B2

(12) United States Patent
Yang et al.

(10) Patent No.: US 12,753,176 B2
(45) Date of Patent: Oct. 6, 2026

(54) COMPOUND, PREPARATION METHOD THEREOF, AND USE THEREOF IN PREPARATION OF ANTI-CANCER DRUG

(71) Applicant: TIANJIN JIKUN MEDICAL TECHNOLOGY CO., LTD., Tianjin (CN)

(72) Inventors: Cheng Yang, The Woodlands, TX (US); Guang Yang, Tianjin (CN); Honggang Zhou, Tianjin (CN); Liang Zhang, Tianjun (CN); Jian Li, Tianjin (CN); Dongchao Lun, Tianjin (CN)

(73) Assignee: TIANJIN JIKUN MEDICAL TECHNOLOGY CO., LTD. (CN)

( * ) Notice: Subject to any disclaimer, the term of this patent is extended or adjusted under 35 U.S.C. 154(b) by 578 days.

(21) Appl. No.: 17/915,817

(22) PCT Filed: Sep. 24, 2021

(86) PCT No.: PCT/CN2021/120046
§ 371 (c)(1),
(2) Date: Sep. 29, 2022

(87) PCT Pub. No.: WO2022/127261
PCT Pub. Date: Jun. 23, 2022

(65) Prior Publication Data

US 2023/0159537 A1 May 25, 2023

(30) Foreign Application Priority Data

Dec. 16, 2020 (CN) ........................ 202011483614.1

(51) Int. Cl.
*C07D 487/04* (2006.01)
*A61K 31/519* (2006.01)
*A61P 35/00* (2006.01)

(52) U.S. Cl.
CPC ............ *C07D 487/04* (2013.01); *A61P 35/00* (2018.01)

(58) Field of Classification Search
CPC ...... C07D 487/04; A61P 35/00; A61K 31/519
See application file for complete search history.

(56) References Cited

U.S. PATENT DOCUMENTS

2019/0367520 A1* 12/2019 Duan .................. C07D 405/12

FOREIGN PATENT DOCUMENTS

CN 103319488 A 9/2013
CN 106928231 A 7/2017
(Continued)

OTHER PUBLICATIONS

Wei, Y. et al. J. Med. Chem. 2021, 64, 9078-9099 (Year: 2021).*
(Continued)

*Primary Examiner* — Clinton A Brooks
*Assistant Examiner* — Kendall Nicole Heitmeier
(74) *Attorney, Agent, or Firm* — C. Tumey Law Group PLLC

(57) ABSTRACT

The present disclosure relates to a pyrazolo[3,4-d]pyrimidine compound, a preparation method thereof, and use thereof in the preparation of an anti-tumor drug. This class of compound has an inhibitory effect on FGFR1-3 and exhibits an anti-proliferation effect on NCI-H1581 and SNU-16 cancer cell lines.

(Continued)

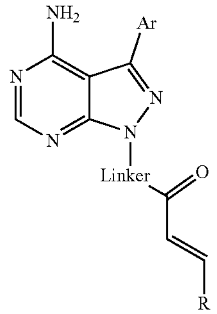

(I)

9 Claims, 4 Drawing Sheets

(56) References Cited

FOREIGN PATENT DOCUMENTS

| | | | | |
|---|---|---|---|---|
| CN | 107513068 | A | * 12/2017 | .......... C07D 405/12 |
| CN | 109369654 | A | 2/2019 | |
| CN | 109970740 | A | 7/2019 | |
| CN | 111018865 | A | 4/2020 | |
| CN | 112574216 | A | 3/2021 | |
| CN | 113264937 | A | 8/2021 | |
| WO | 2013102059 | A1 | 7/2013 | |
| WO | 2017114383 | A1 | 7/2017 | |
| WO | 2019034075 | A1 | 2/2019 | |

OTHER PUBLICATIONS

Krook, M. A. et al. British Journal of Cancer. 2021, 124, 880-892. (Year: 2021).*

He, L., et al. Eur. J. Med. Chem. 2018, 145, 96-112 (Year: 2018).*

Turner, Nicholas et al. "Fibroblast growth factor signalling: from development to cancer." Feb. 2010, vol. 10. www.nature.com/reviews/cancer, pp. 116-129.

Carter, Edward P. et al. "Careless talk costs lives: fibroblast growth factor receptor signalling and the consequences of pathway malfunction." Trends in Cell Biology, Apr. 2015, vol. 25, No. 4, pp. 221-233. https://dx.doi.org/10.1016/j.tcb.2014.11.003.

Touat, Mehdi et al. "Targeting FGFR Signaling in Cancer." Clin Cancedr Res. 21(12) Jun. 15, 2015, pp. 2684-2964.

Dieci, Maria Vittoria et al. "Fibroblast Growth Factor Receptor Inhibitors as a Cancer Treatment: From a Biologic Rationale to Medical Perspectives." Cancer Discovery, Mar. 2013, pp. 264-279. www.aacrjournals.org, doi: 10.1158/2159-8290.CD-12-0362.

Hagel, Margit et al. "First Selective Small Molecular Inhibitor of FGFR4 for the Treatment of Hepatocellular Carcinomas with an Activated FGFR4 Signaling Pathway." Cancer Discovery, Apr. 2015, pp. 524-437. http://aacrjournals.org/cancerdiscovery/article-pdf/5/4/424/1822156/424.pdf.

Babina, Irina S. et al. "Advances and challenges in trageting FGFR signalling in cancer." Nature Reviews, May 2017, vol. 17, www.nature,com/nrc. doi:10.1038/nrc.2017.8.

Renhowe, Paul A. et al. "Design, Structure-Activity Relationships and in Vivo Characterization of 4-Amino-3-benzimidazol-2-ylhydroquinolin-2-ones: A Novel Class of Receptor Tyrosine Kinase Inhibitors." Journal of Medical Chemistry, 2009, vol. 52, No. 2, pp. 278-292.

Bello, Ezia et al. "E-3810 Is a Patent Dual Inhibitor of VEGFR and FGFR that Exerts Antihumor Activity in Multiple Preclinical Models." Cancer Res. 71(4) Feb. 15, 2001. downloaded from cancerres.aacrjournals.org (Mar. 29, 2015), pp. 1396-1405.

Roth, Gerald J. et al. Design, Synthesis and Evaluation of Indolinones as TripleAngiokinase Inhibitors and the Discovery of a High Specific 6-Methoxycarbonyl-Substituted Indolinone (BIBF 1120). Journal of Medicinal Chemistry, 2009, vol. 52, No. 14, pp. 4466-4480. doi: 10.1021/jm900431g.

Gozgit, Joseph M. et al. Ponatinib (AP24534), a Multitargeted Pan-FGFR Inhibitor with Activity in Multiple FGFR-Amplified or Mutated Cancer Models. Mol Cancer Ther, 11(3) Mar. 2012, pp. 690-699. doi: 10.1158/1535-7163.MCT-11-0450.

Gavine, Paul R. et al. "AZD4547: An Orally Bioavailable, Potent, and Selective Inhibitor of the Fibroblast Growth Factor Receptor Tyrosine Kinase Family." Cancer Res, 72(8) Apr. 15, 2012, pp. 2045-2056. DOI: 10.1158/0008-5472.CAN-11-3034.

Guagnano, Vito et al. "Discovery of 3-(2,6-Dichloro-3m5-dimethoxy-phenyl)-1-{6-[4-(4-ethyl-piperazin-1-yl)-phenylamino]-pyrimidin-4-yl]-1-methyl-urea (NVP-BGJ398), A Potent and Selective Inhibitor of the Fibroblast Growth Factor Receptor Family of Receptor Tyrosine Kinase." J. Med. Chem. 2011, 54, pp. 7066-7083.

Zhao, Genshi et al. "A Novel, Selective Inhibitor of Fibroblast Growth Factor Receptors That Shows a Potent Broad Spectrum of Antitumor Activity in Several Tumor Xenograft Models." Mol Cancer Ther 10(11) Nov. 2011, pp. 2200-2011. DOI: 10.1158/1535-7163.MCT-11-0306.

Perera, Timothy P.S. et al. "Discovery and Pharmacological Characterization of JNJ-42756493 (Erdafitinib), a Functionally Selective Small-Molecule FGFR Family Inhibitor." Mol Cancer Ther 16(6) Jun. 2017, pp. 1010-1020. http:/aacrjournals.org/mvt/article-pdf/16/6/1010/1855211/1010.pdf.

Zhou, Wenjun et al. "A Structure-Guided Approach to Creating Covalent FGFR Inhibitors." Chemistry & Biology 17, 285-295, Mar. 26, 2010. DOI 10.1016/j.chembiol.2010.02.007.

Tan, Li et al. "Development of covalent inhibitors that can overcome resistance to first-generation FGFR kinase inhibitors." Published online Oct. 24, 2014, E4869-E4877. www.pnas.org/cgi/doi/10.1073/pnas.1403438111.

Brown, Wells S. et al. "Covalent Targeting of Fibroblast Growth Factor Receptor Inhibits Metastatic Breast Cancer." Mol Cancer Ther 15(9) Sep. 2016, pp. 2096-2106. http://aacrjournals.org/mvt/article-pdf/15/9/2096/2333950/2096.pdf.

Brameld, Ken A. et al. "Discovery of the Irreversible Covalent FGFR Inhibitor 8-(3-(4-Acryloylpiperazin-1-yl)propyl)-6-(2,6-dichloro-3,5-dimethoxyphenyl)-2-(methylamino)pyrido[2,3-d]pyrimidin-7(8H)-one (PRN1371) for the Treatment of Solid Tumors." J. Med. Chem. 2017,60, 6516-6527. DOI: 10.1021/acs.jmedchem.7b00360.

Wang, Yulan et al. "Discovery and Development of a Series of Pyrazolo[3,4-d] pyridazinone Compounds as the Novel Covalent Fibroblast Growth Factor Receptor Inhibitors by the Rational Drug Design." J. Med. Chem. 2019, 62,7473-7488. DOI: 10.1021/acs.jmedchem.9b00510.

Wang, Yulan et al. "Discovery of Potent Irreversible Pan-Fibroblast Growth Factor Receptor (FGFR) Inhibitors." J. Med. Chem. 2018, 61m 9085-9104. DOI: 10.1021/acs.jmedchem.7b01843.

Li, Xueqiang et al. "2-Oxo-3, 4-dihydropyrimido[4,5-d]pyrimidinyl derivatives as new irreversible pan fibroblast growth factor receptor (FGFR) inhibitors." European Journal of Medicinal Chemistry 135 (2017) 531-543. pp. 531-543. http://dx.doi.org/10.1016/j.ejmech.2017.04.049.

He, Linhong et al. "Design, synthesis and biological evaluation of 7H-pyrrolo[2,3-d] pyrimidin-4-amine derivatives as selective Btk inhibitors with improved pharmacokinetic properties for the treatment of rheumatoid arthritis." European Journal of Medicinal Chemistry 145 (2018) 96-112. https://doi.org/10.1016/j.emech.2017.12.079.

CAS Registration. Reg. No. 1772577-86-2, Jun. 3, 2015, American Chemical Society.

International Search Report issued Dec. 28, 2021 in priority PCT application No. PCT/CN/2021/120046.

* cited by examiner

COMPOUND, PREPARATION METHOD THEREOF, AND USE THEREOF IN PREPARATION OF ANTI-CANCER DRUG

CROSS REFERENCE TO RELATED APPLICATIONS

The present disclosure is a national phase application of PCT/CN2021/120046 filed Sep. 24, 2021, which claims priority to the Chinese Patent Application 202011483614.1 filed to the China National Intellectual Property Administration (CNIPA) on Dec. 16, 2020 and entitled "COMPOUND, PREPARATION METHOD THEREOF, AND USE THEREOF IN PREPARATION OF ANTI-CANCER DRUG", which is incorporated herein by reference in its entirety.

TECHNICAL FIELD

The present disclosure relates to the technical field of pharmacy, and in particular to a 2H-pyrazolo[3,4-d]pyrimidine derivative, a preparation method thereof, and use thereof in the preparation of an anti-cancer drug.

BACKGROUND ART

Fibroblast growth factor receptors (FGFRs) are members of the receptor tyrosine kinase (RTK) family and are receptor protein tyrosine kinases (RPTKs), including four highly-conserved transmembrane tyrosine kinases: FGFR1, FGFR2, FGFR3, and FGFR4. A signaling pathway of FGFR is that a ligand binds to a receptor to induce FGFR dimerization, thereby causing cascade activation of downstream signaling pathways such as Ras-MAPK, PI3K-Akt, STAT, and PLCγ. FGFRs play important roles in a variety of cell functions, such as cell proliferation and differentiation, and biological processes including development, angiogenesis, homeostasis, and wound repair. According to research surveys[1-3], 7.1% of cancer patients have FGFR abnormalities. For example, the FGFR1 amplification occurred most in squamous non-small cell lung cancer (NSCLC) patients with a proportion of 20%, which was 10% in breast cancer patients, 5% in ovarian cancer patients, and 3% in bladder cancer patients. Currently, FGFR2 mutations have been found in gastric cancer (10%), endometrial cancer (12%), squamous NSCLC (5%), and triple-negative breast cancer (TNBC) (4%); and FGFR3 mutations are well known in bladder cancer (50% to 60%) and myeloma (15% to 20%). Aberrant FGF19/FGFR4 signaling is closely associated with hepatocellular carcinoma (HCC). Therefore, the development of a novel selective FGFR inhibitor to block the FGF/FGFR signaling pathway presents a promising therapeutic strategy for FGFR-associated cancer[4-5].

Researchers are committed to developing an FGFR inhibitor as a novel anti-cancer agent for the treatment of FGFR-associated cancer. Several multi-targeted tyrosine kinase inhibitors (TKIs) are initially used to treat FGFR abnormality-associated cancer[6], such as dovitinib (TKI-258), lucitanib (E-3810)[7], nintedanib (BIBF-1120)[8], and ponatinib (AP-24534)[9]. These FGFR inhibitors developed early are non-selective[10]. Subsequently, several TKIs selective for FGFR with various scaffolds are developed. Some TKIs are currently in different stages of clinical research, such as AZD-4547 (phase III)[11], BGJ-398 (phase II)[12], LY-2874455 (phase II)[13], and JNJ-42756493 (phase II)[14], and these selective FGFR inhibitors are ATP-competitive inhibitors that bind to an active form of FGFR. In addition, FGFR inhibitors developed by many pharmaceutical chemistry laboratories have been reported.[15-21].

SUMMARY

The technical problems to be solved/objectives to be achieved by the present disclosure at least include: overcoming the defects in the prior art and providing a 2H-pyrazolo[3,4-d]pyrimidine derivative, a preparation method thereof, and use thereof in the preparation of an anti-cancer drug.

In order to achieve the above objectives, the present disclosure discloses the following technical solutions:

The present disclosure provides a compound of formula I or a pharmaceutically acceptable salt thereof:

formula I

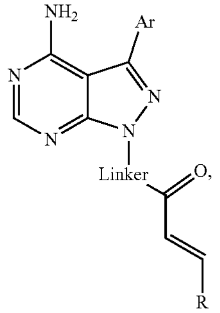

where Ar is any one selected from the group consisting of a substituted aryl and a substituted heterocyclic group;

R is any structure selected from the group consisting of H, alkyl, aryl, —$CF_3$, and an alkyl tertiary amine; and Linker is any one selected from the group consisting of alkyl, alkoxyl, a heteroatom substituent, and a substituted N-heterocyclic ring.

In some embodiments, the Ar is

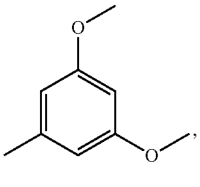,

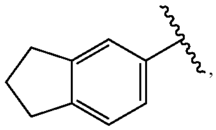,

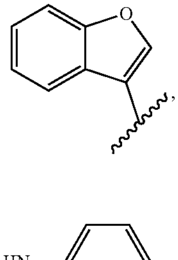,

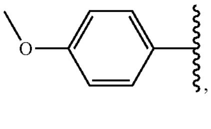,

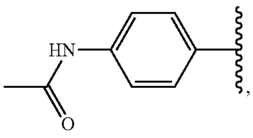,

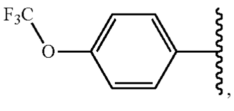,

-continued
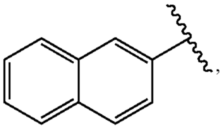,
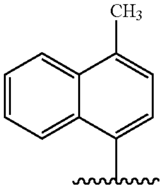,
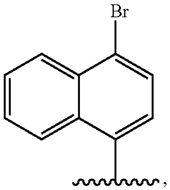,
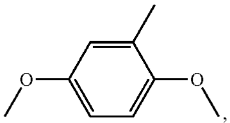,
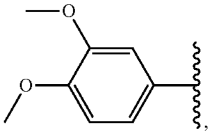,
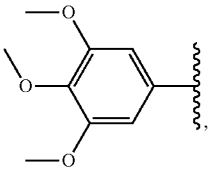,
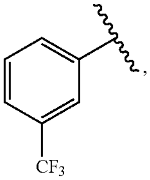,
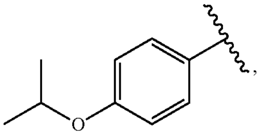,
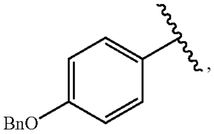,
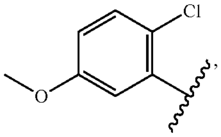,
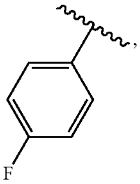,
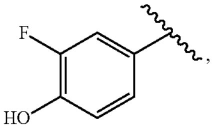,
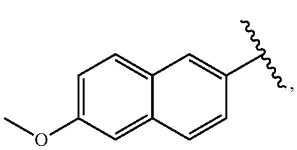,
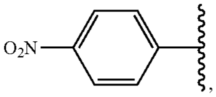,
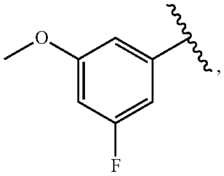,
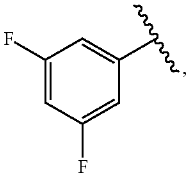,
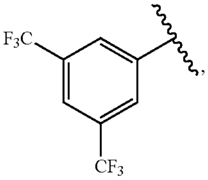,
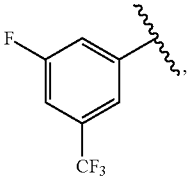,
-continued
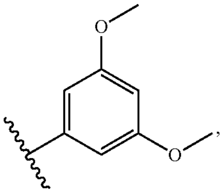,
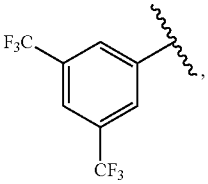,
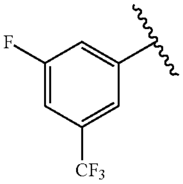
or
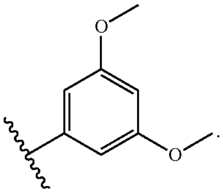.
In some embodiments, the R is H, $CF_3$, $(CH_3)_2NCH_2$, or $CH_3$.
In some embodiments, the Linker is
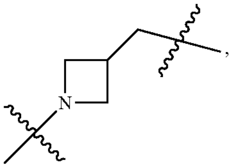,
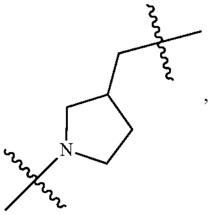,
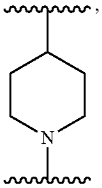,
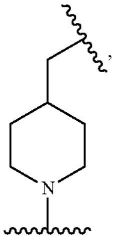,
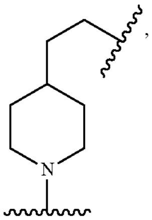,
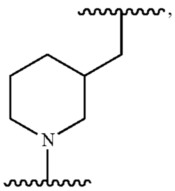,
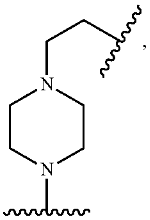,
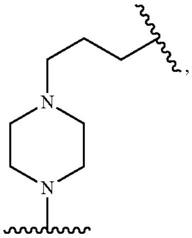,
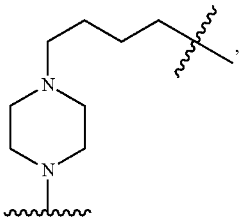, -continued
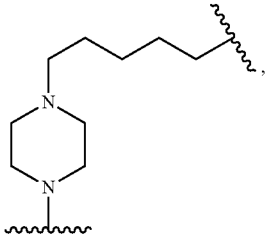
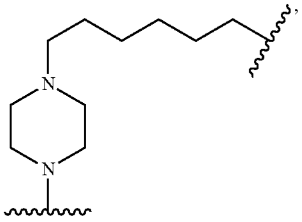
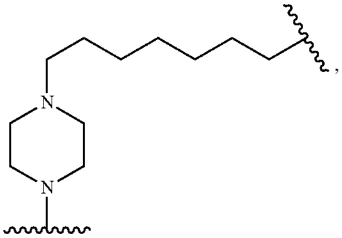
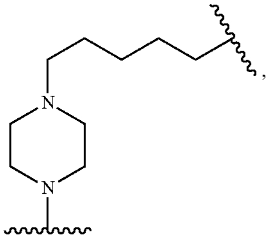
or
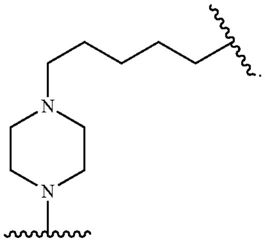
In some embodiments, the compound is one selected from the group consisting of compound 1 to compound 40:
compound 1
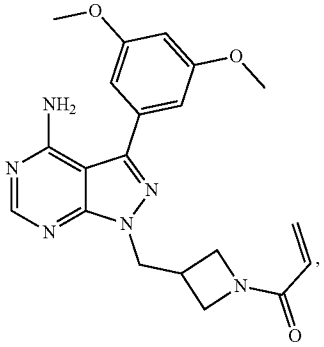
-continued
compound 2
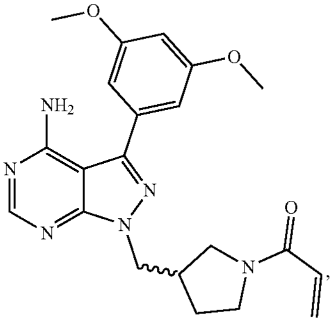
compound 3
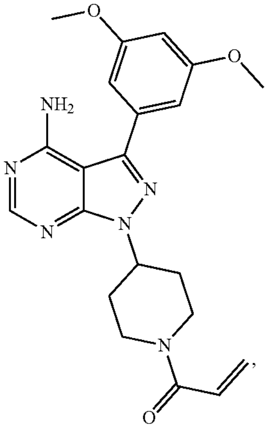
compound 4
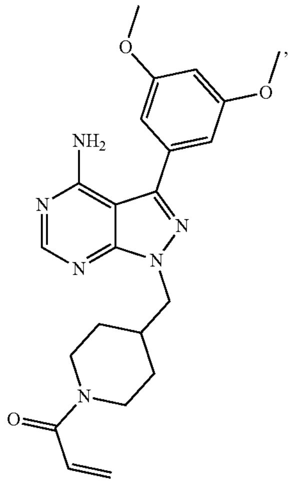

-continued
compound 5
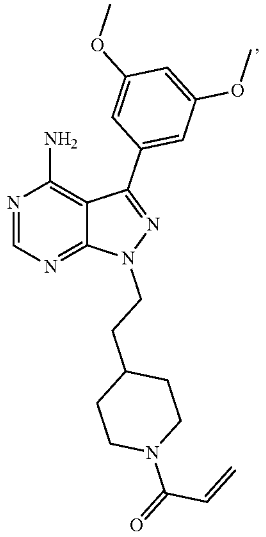
compound 6
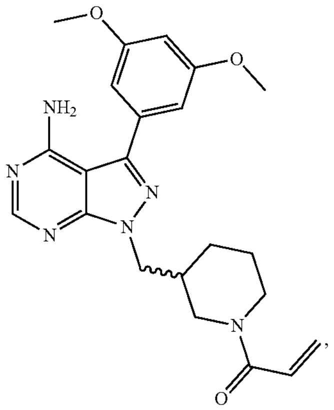
compound 7
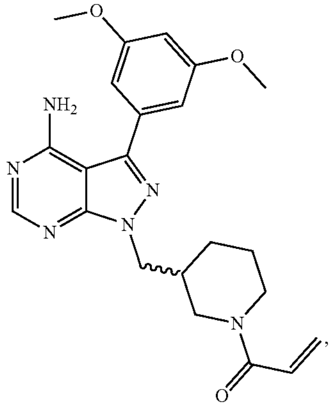
-continued
compound 8
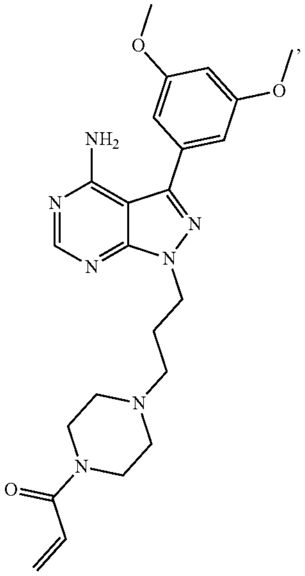
compound 9
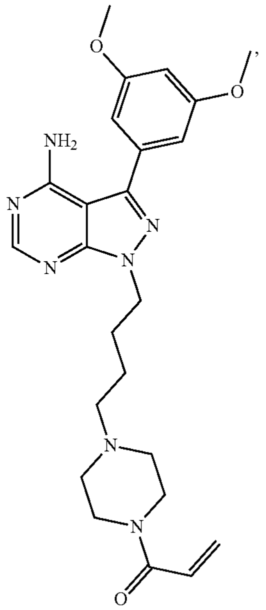

-continued
compound 10
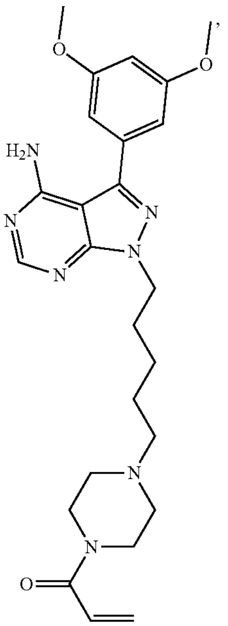
compound 11
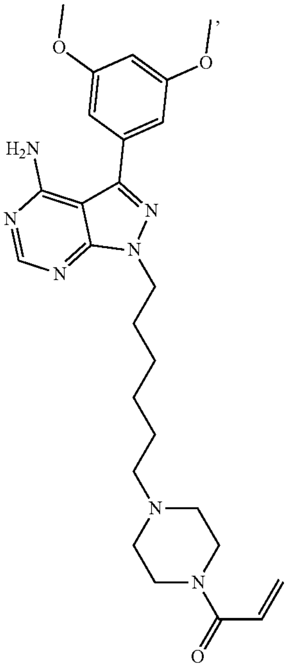
-continued
compound 12
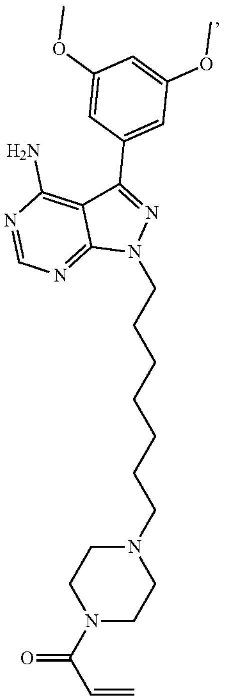
compound 13
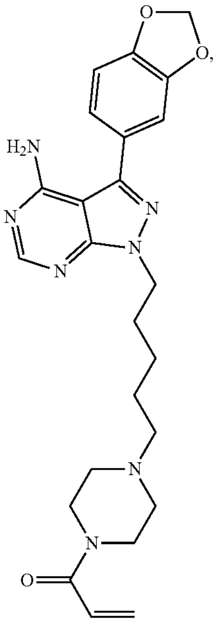

-continued
compound 14
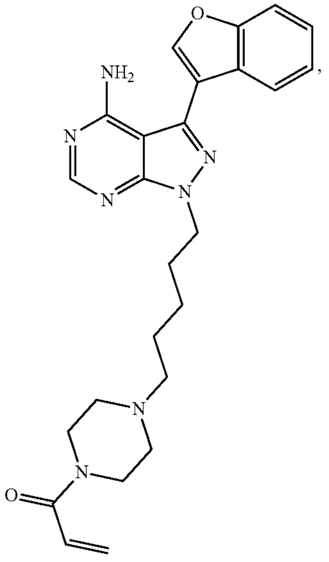
compound 15
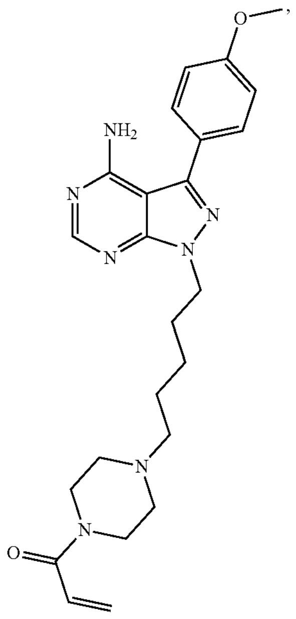
-continued
compound 16
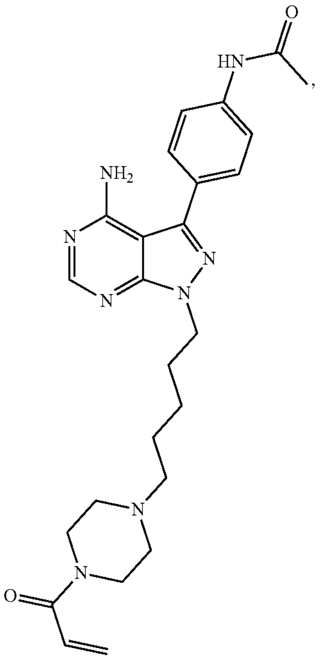
compound 17
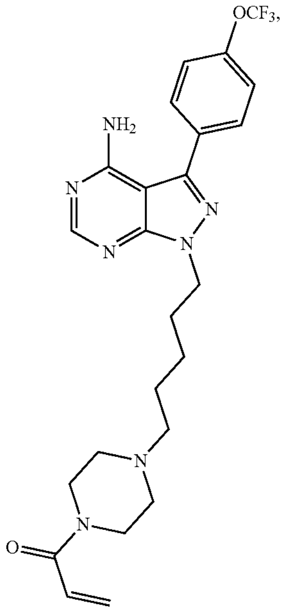

-continued
compound 18
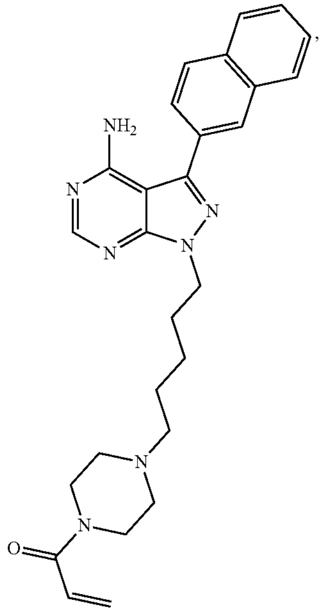
compound 19
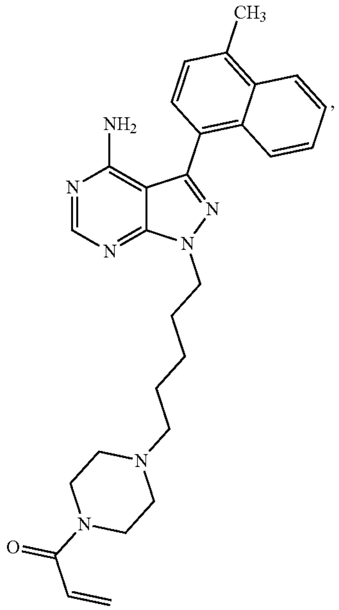
-continued
compound 20
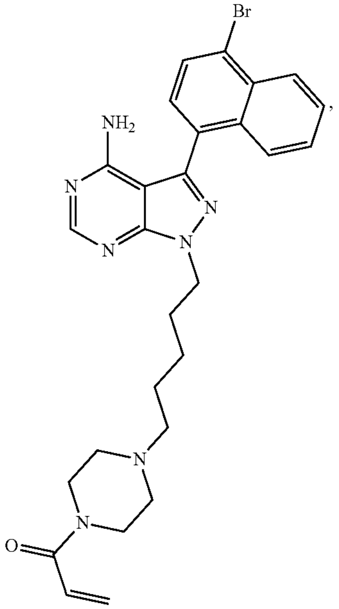
compound 21
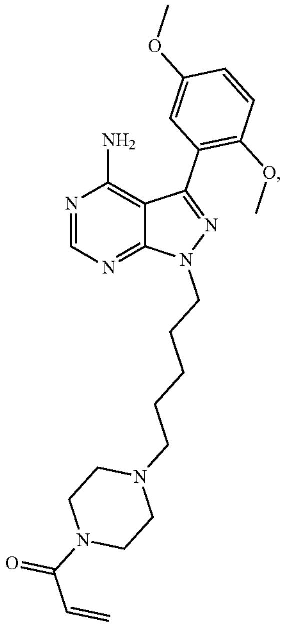

compound 22
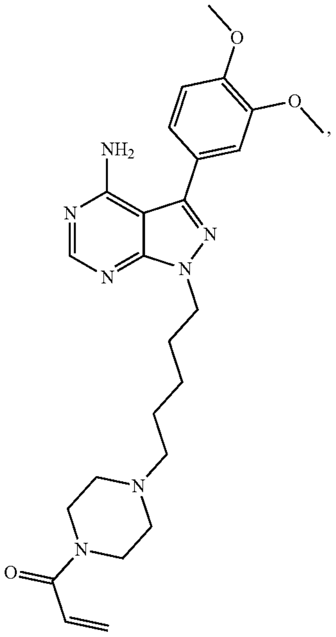
compound 23
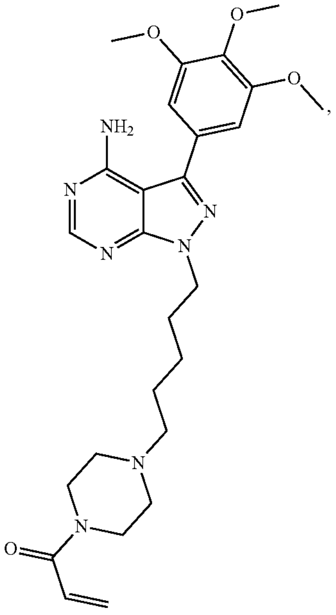
compound 24
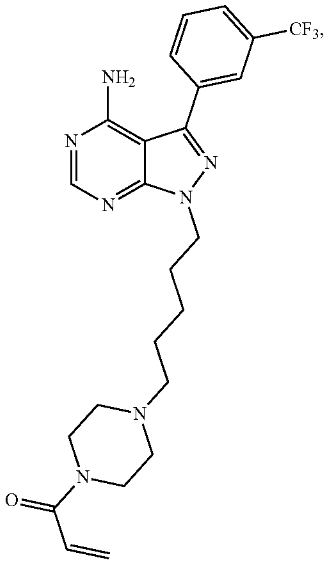
compound 25
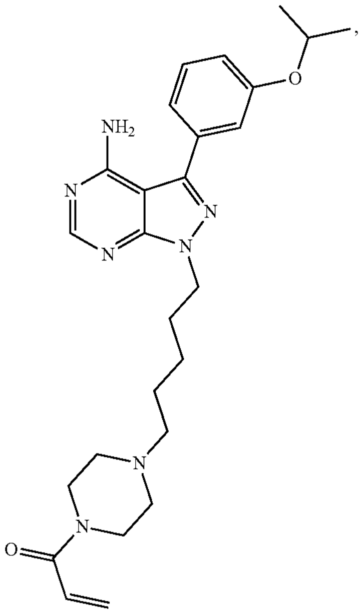

compound 26
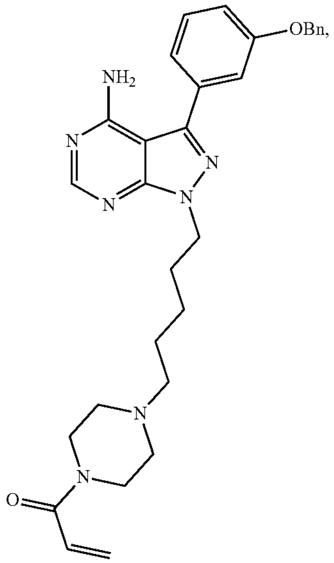
compound 27
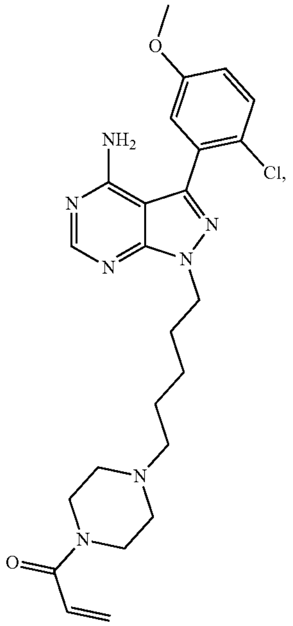
compound 28
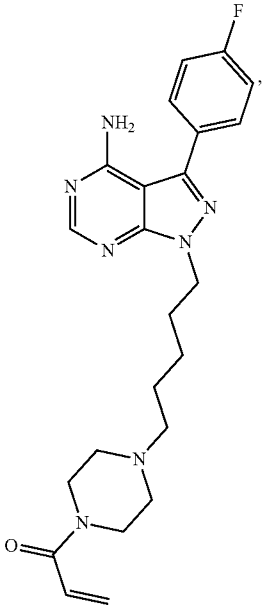
compound 29
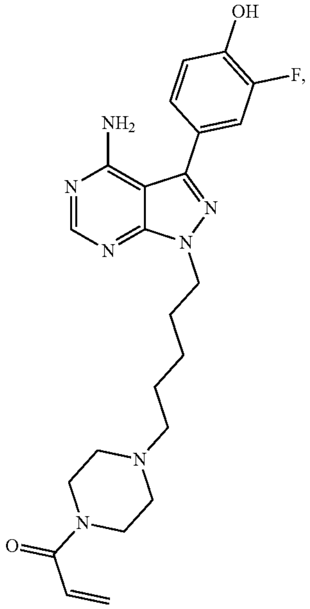

-continued
compound 30
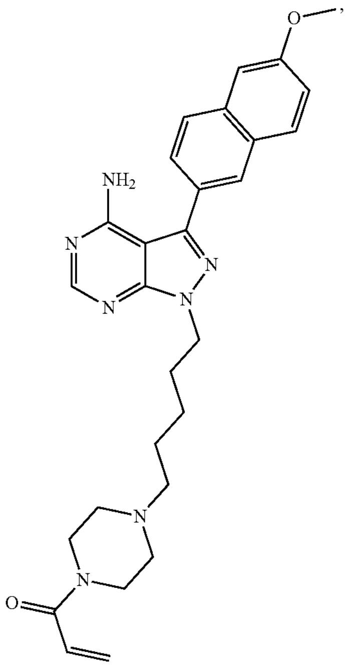
compound 31
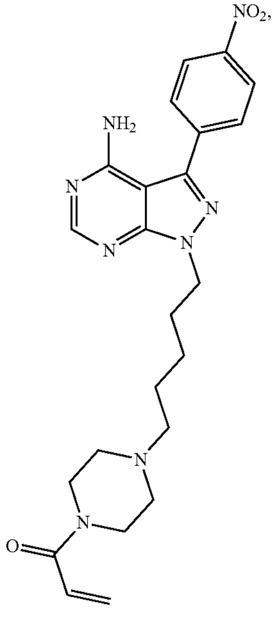
-continued
compound 32
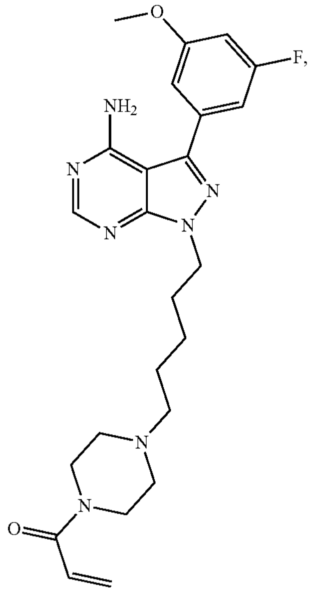
compound 33
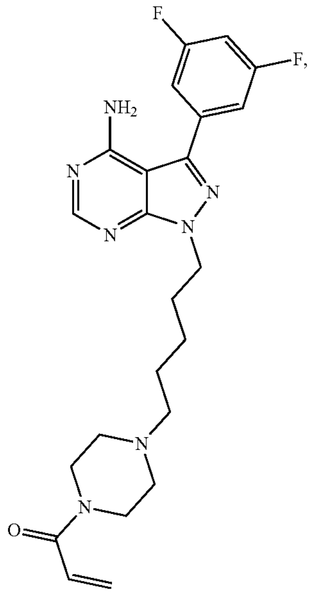

-continued
compound 34
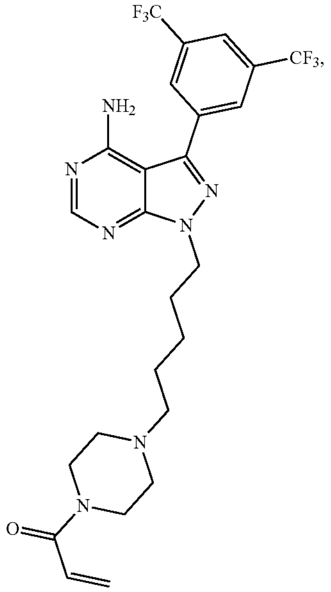
compound 35
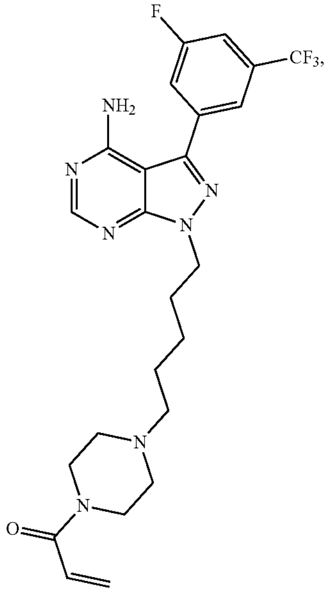
-continued
compound 36
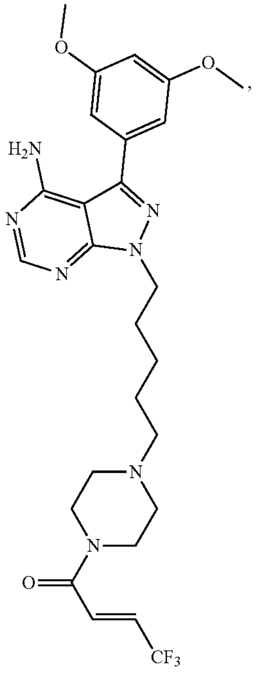
compound 37
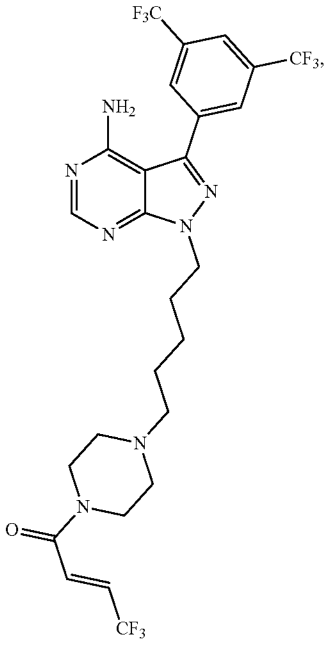

-continued
compound 38
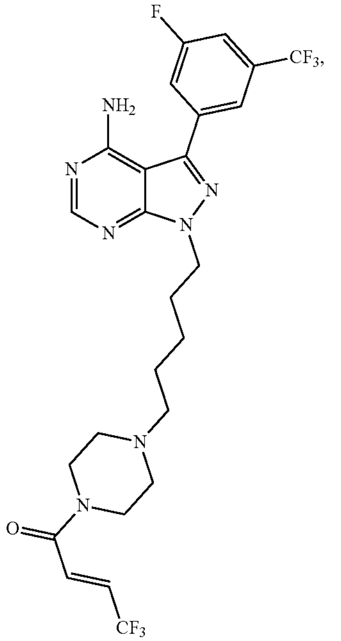
compound 39
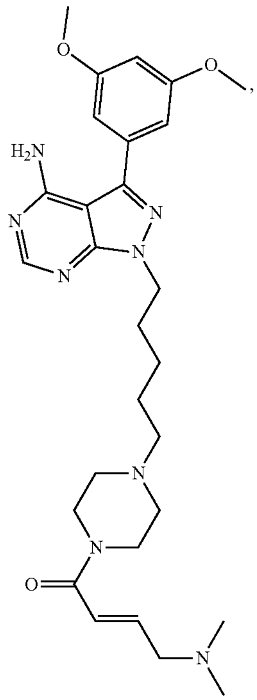
and
-continued
compound 40
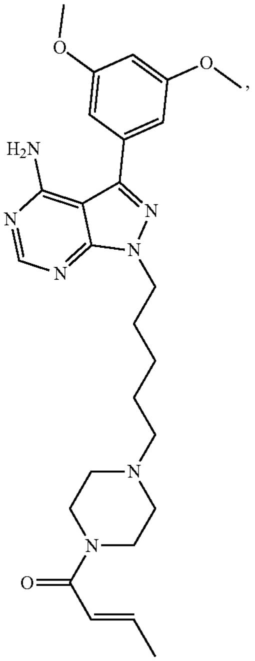
The present disclosure also provides a preparation method of the compound or the pharmaceutically acceptable salt thereof according to the above technical solution, with a synthetic route as follows:
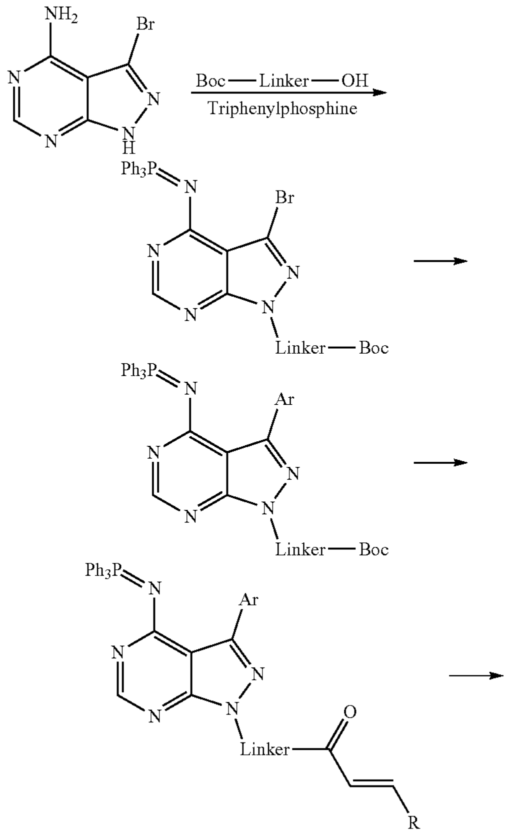

-continued

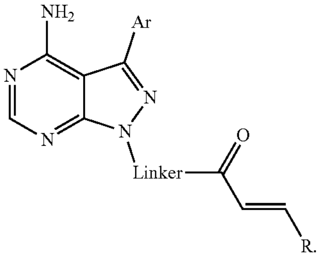

In some embodiments, the preparation method may include the following steps:

subjecting a compound with a structure shown in formula a and a compound with a structure shown in formula b to a Mitsunobu reaction at room temperature for 4 h to obtain a compound with a structure shown in formula c;

subjecting the compound with the structure shown in formula e and trifluoroacetic acid (TFA) to a first deprotection reaction at 0° C., and then subjecting a resulting material to an acylation reaction at room temperature to obtain a compound with a structure shown in formula f; and subjecting the compound with the structure shown in formula f to a second deprotection acylation reaction at room temperature to obtain the compound with a structure shown in formula I;

formula a

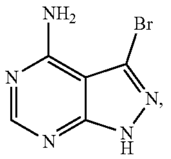

formula b

Boc—Linker—OH, formula c

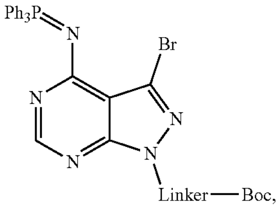

formula d

Ar—$B(OH)_2$, formula e

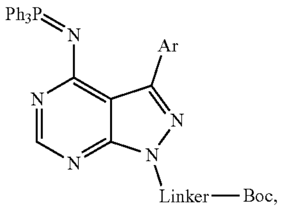

and

-continued formula f

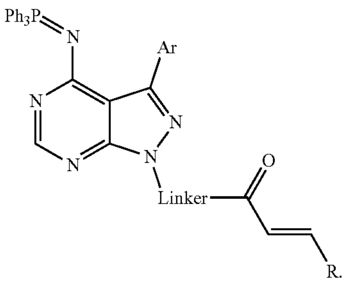

The present disclosure also provides use of the compound or the pharmaceutically acceptable salt thereof according to the above technical solution in the preparation of an tumor cell proliferation inhibitor, where a tumor cell is an FGFR abnormality-associated tumor cell.

In some embodiments, the tumor cell includes NCI-H1581 or SNU-16.

The present disclosure also provides use of the compound or the pharmaceutically acceptable salt thereof according to the above technical solution in blocking a fibroblast growth factor (FGF)/FGFR signaling pathway in a tumor cell, where the tumor cell is an FGFR abnormality-associated tumor cell.

In some embodiments, the tumor cell includes NCI-H1581 or SNU-16.

The present disclosure also provides a pharmaceutical composition including the compound or the pharmaceutically acceptable salt thereof according to the above technical solution, where the pharmaceutical composition further includes one or more pharmaceutically acceptable excipients; and a dosage form of the pharmaceutical composition is any pharmaceutically acceptable dosage form.

The present disclosure also provides use of the compound or the pharmaceutically acceptable salt thereof according to the above technical solution or the pharmaceutical composition according to the above technical solution in the preparation of a drug for treating and/or preventing a cancer.

In some embodiments, the cancer is an FGFR abnormality-associated cancer.

The present disclosure also provides use of the pharmaceutical composition according to the above technical solution in the preparation of an irreversible pan-FGFR inhibitor.

The present disclosure also provides a method for treating a cancer, including the following step:

administering an anti-cancer drug to a patient through oral administration or intraperitoneal injection, where the anti-cancer drug includes the compound or the pharmaceutically acceptable salt thereof according to the above technical solution.

In some embodiments, the anti-cancer drug includes the compound 10 or the compound 36.

In some embodiments, the anti-cancer drug is administered at a dose of 50 mg/kg or 100 mg/kg; and the dose is calculated according to a dosage of the compound 10 or the compound 36.

In some embodiments, when the anti-cancer drug includes the compound 10, the anti-cancer drug is administered orally.

In some embodiments, when the anti-cancer drug includes the compound 36, the anti-cancer drug is administered through intraperitoneal injection.

In the present disclosure, the term "pharmaceutically acceptable adjuvant" includes pharmaceutically acceptable carriers, excipients, diluents, and the like, which are compatible with the active pharmaceutical ingredients. The preparation of a pharmaceutical formulation with a pharmaceutically acceptable adjuvant is well known to those of ordinary skill in the art.

In the present disclosure, the pharmaceutical composition may be combined with a pharmaceutically acceptable adjuvant (such as a carrier, an excipient, a diluent, or the like well known to those of ordinary skill in the art) to prepare various formulations, in further embodiments, the formulations include solid formulations and liquid preparations, such as tablets, pills, capsules, powders, suspensions, granules, syrups, emulsions, suspensions, and various sustained-release dosage forms, in some embodiments, the formulations is administered orally.

BRIEF DESCRIPTION OF DRAWINGS

FIG. 1A shows the inhibition on the activation of the FGFR1 and the downstream signaling pathway thereof in NCI-H1581 cells, and FIG. 1B shows the inhibition on the activation of the FGFR2 and the downstream signaling pathway thereof in SNU-16 cells;

FIG. 2A shows the inhibition on the activation of the FGFR1 and the downstream signaling pathway thereof in NCI-H1581 cells, and FIG. 2B shows the inhibition on the activation of the FGFR2 and the downstream signaling pathway thereof in SUN-16 cells;

DETAILED DESCRIPTION OF THE EMBODIMENTS

Figure 1:
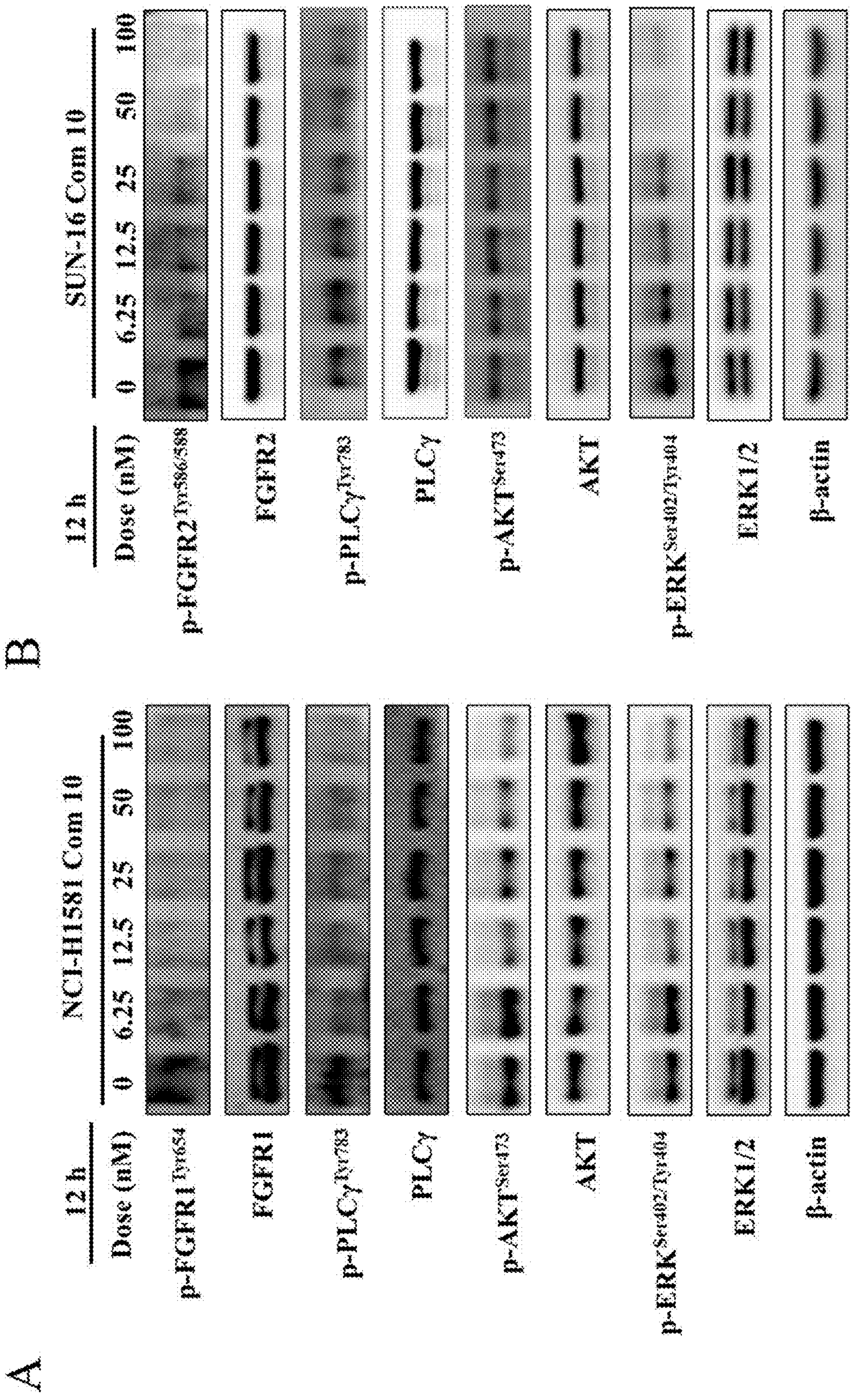
FIGS. 1A and 1B show that the compound 10 inhibits the activation of FGFR1 and a downstream signaling pathway thereof in NCI-H1581 cells and inhibits the activation of FGFR2 and a downstream signaling pathway thereof in SNU-16 cells in a concentration gradient-dependent manner, where

Unless otherwise defined, the technical terms used in the following examples have the same meanings as commonly understood by those skilled in the art to which the present disclosure belongs. Unless otherwise specified, in the following examples, the test reagents used are all conventional biochemical reagents, and the test methods are all conventional methods.

The present disclosure will be described in detail below with reference to the examples.

Example 1: Preparation of Compound 1 compound 1

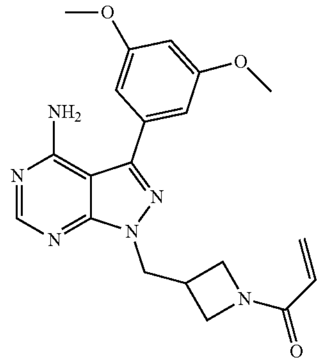

A specific preparation method was as follows:

1) Preparation of Compound (1-1)

compound (1 - 1 )

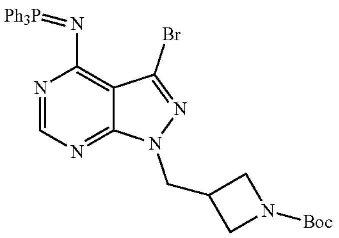

3-Bromo-1H-pyrazolo[3,4-d]pyrimidin-4-amine (500 mg, 2.34 mmol) was dissolved in dry tetrahydrofuran (THF) (23 mL), and then triphenylphosphine (TPP) (2.08 g, 7.94 mmol) and 1-Boc-3-azetidinemethanol were added; diisopropyl azodiformate (DIAD) (1.60 g, 7.94 mmol) was added dropwise at 0° C. under the protection of argon, then the temperature was slowly raised to room temperature, and a reaction was further allowed for 4 h; and a reaction solution was spin-dried and purified by column chromatography (petroleum ether:ethyl acetate=5:1 to 2:1) to obtain the compound 1-1 (yellow oily liquid, 685 mg, 69%).

Nuclear magnetic resonance (NMR) test results of the compound 1-1 were as follows:

$^1$H NMR (400 MHz, $CDCl_3$) δ 8.06 (s, 1H), 7.96-7.87 (m, 6H), 7.64-7.45 (m, 9H), 4.48 (d, J=7.3 Hz, 2H), 3.97 (t, J=8.5 Hz, 2H), 3.88-3.74 (m, 2H), 3.19-2.98 (m, 1H), 1.41 (s, 9H). $^{13}$C NMR (100 MHz, $CDCl_3$) δ 163.1, 163.0, 156.2, 155.9, 154.6, 154.5, 133.4, 133.4, 133.3, 133.3, 132.4, 132.3, 132.2, 128.8, 128.7, 128.7, 128.6, 128.6, 128.5, 128.4, 127.8, 127.4, 120.9, 107.1, 79.3, 52.9, 51.5, 49.7, 28.8, 28.4, 21.7, 14.2. HRMS (ESI) calculated for $C_{32}H_{32}BrN_6NaO_2P^+$: 665.1400, found 665.1402.

2) Preparation of Compound (1-2)

compound (1-2)

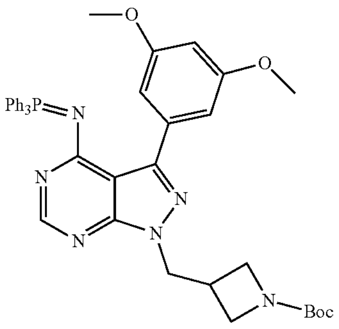

The compound 1-1 (5.01 mg, 6.74 mmol) and 3,5-dimethoxyphenylboronic acid (1.59 g, 8.76 mmol) were dissolved in a mixed solution of 1,4-dioxane and water (9 mL, v:v=3:1), and then potassium carbonate (1.87 g, 13.5 mmol) and $Pd(PPh_3)_4$ (778 mg, 0.674 mmol) were added; a resulting system was argon replaced three times, and then heated to 80° C. in an oil bath to undergo a reaction overnight; and after the reaction was completed, a resulting reaction system was washed with saturated sodium chloride (270 mL) and then subjected to extraction with ethyl acetate (90 mL), and a resulting organic phase was dried, concentrated, and purified by column chromatography (dichloromethane (DCM):methanol=70:1 to 30:1) to obtain the compound 1-2 (yellow oily liquid, 4.3 g, 60%).

NMR test results of the compound 1-2 were as follows: $^1$H NMR (400 MHz, $CDCl_3$) δ 8.06 (d, J=3.2 Hz, 1H), 7.89-7.71 (m, 6H), 7.56-7.40 (m, 11H), 6.70-6.41 (m, 1H), 4.58 (dd, J=7.3, 3.2 Hz, 2H), 4.11-3.96 (m, 2H), 3.92-3.84 (m, 2H), 3.76 (d, J=3.1 Hz, 6H), 3.26-3.07 (m, 1H), 1.41 (d, J=3.1 Hz, 9H). $^{13}$C NMR (100 MHz, $CDCl_3$) δ 163.9, 163.9, 163.5, 163.4, 160.3, 156.3, 156.3, 155.2, 154.7, 146.1, 135.6, 134.2, 133.5, 133.4, 133.4, 133.3, 132.3, 132.2, 132.0, 132.0, 132.0, 1292, 128.6, 128.6, 128.5, 128.5, 128.4, 128.4, 128.2, 128.2, 127.8, 107.9, 100.6, 79.3, 77.4, 55.3, 49.5, 28.9, 28.4, 24.5. HRMS (ESI) calculated for $C_{40}H_{41}N_6NaO_4P^+$: 723.2819, found 723.2822.

3) Preparation of Compound (1-3)

compound (1-3)

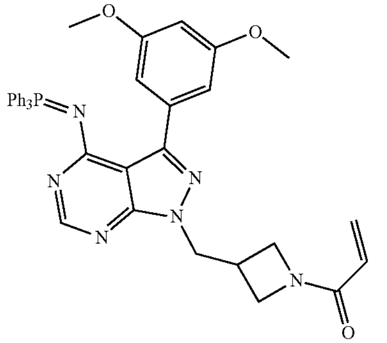

At 0° C., the compound 1-2 (450 mg, 0.587 mmol) was dissolved in DCM (5 mL), and then TFA (5 mL) was slowly added dropwise, after 30 min the reaction was completed; adjusting alkali of a resulting reaction solution was conducted with saturated $NaHCO_3$, and a resulting organic phase was concentrated to dry to obtain a brown-yellow oily intermediate. At 0° C., the intermediate was dissolved in 5 mL of DCM, then triethylamine (TEA) (98.2 μL, 0.704 mmol) was added, and then acryloyl chloride (52.2 μL, 0.646 mmol) was added dropwise; and a reaction was further allowed for 1 h at room temperature; and when it was monitored by thin layer chromatography (TLC) that the reaction was completed, a resulting reaction system was washed with saturated NaCl and then subjected to extraction with ethyl acetate, and a resulting organic phase was dried, concentrated, and purified by column chromatography (DCM:methanol=30:1 to 10:1) to obtain the compound 1-3 (yellow oily liquid, 78 mg, 72%).

4) Preparation of Compound 1: The compound 1-3 (100 mg, 0.189mmol) was added to a mixed solution of acetic acid, THF, and water (3 mL, 3:1:2), and a reaction was conducted at room temperature for 18 h; and when it was monitored by TLC that the reaction was completed, a pH of a resulting reaction solution was adjusted to 7 to 8 with a saturated $NaHCO_3$ solution (15 mL), extraction was conducted with ethyl acetate (10 mL×2), and a resulting organic phase was dried, concentrated, and purified by column chromatography (DCM: methanol=15:1 to 7:1) to obtain the compound 1 (yellow solid, 57.8 mg, 70%).

NMR test results of the compound 1 were as follows: $^1$H NMR (400 MHz, $CDCl_3$) δ 8.38 (s, 1H), 6.80 (d, J=2.3 Hz, 2H), 6.57 (t, J=2.3 Hz, 1H), 6.33 (dd, J=17.0, 1.9 Hz, 1H), 6.17 (dd, J=17.0, 10.3 Hz, 1H), 5.76-5.57 (m, 3H), 4.76-4.61 (m, 2H), 4.38-4.14 (m, 3H), 4.02 (dd, J=10.5, 5.5 Hz, 1H), 3.87 (s, 6H), 3.49-3.25 (m, 1H). $^{13}$C NMR (100 MHz, $CDCl_3$) δ 165.7, 161.6, 157.8, 156.2, 154.7, 144.7, 134.8, 127.4, 127.2, 125.7, 106.3, 101.2, 98.4, 55.6, 53.5, 50.8, 49.4, 32.7, 29.1, 27.9. HRMS (ESI) calculated for $C_{20}H_{22}N_6NaO_3^+$: 417.1646, found 417.1648.

Example 2: Preparation of Compound 2 compound 2

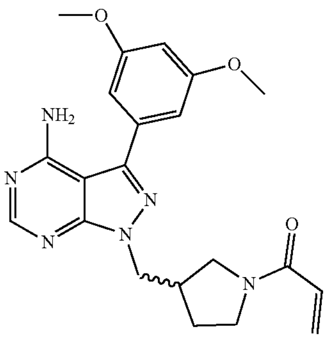

A specific preparation method was the same as the preparation method of compound 1, except that one of the raw materials was equimolar 1-Boc-3-hydroxymethylpyrrolidine, in replacement of 1-Boc-3-azetidinemethanol in the preparation method of compound (1-1). NMR test results of the compound 2 were as follows:

$^1$H NMR (400 MHz, $CDCl_3$) δ 8.38 (s, 1H), 6.81 (d, J=2.2 Hz, 2H), 6.62-6.54 (m, 2H), 6.25 (dd, J=16.9, 2.0 Hz, 1H), 5.76 (s, 2H), 5.66 (dd, J=10.6, 2.0 Hz, 1H), 4.65 (d, J=13.3 Hz, 1H), 4.49 (t, J=7.2 Hz, 2H), 3.99 (d, J=13.7 Hz, 1H), 3.86 (s, 6H), 3.00 (t, J=12.6 Hz, 1H), 2.64-2.52 (m, 1H), 1.97-1.94 (m, 1H), 1.91 (s, 2H). $^{13}$C NMR (100 MHz, $CDCl_3$) δ 164.5, 161.5, 158.0, 156.0, 154.6, 144.6, 134.9, 128.5, 127.5, 106.4, 101.3, 98.3, 55.6, 50.0, 49.1, 45.7, 45.2, 39.9, 37.74 29.6, 27.9. HRMS (ESI) calculated for $C_2H_{24}N_6NaO_3^+$: 431.1802, found 431.1804.

Example 3: Preparation of Compound 3 compound 3

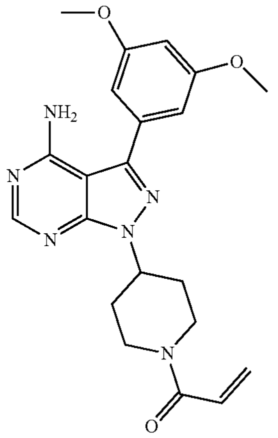

A specific preparation method was the same as the preparation method of compound 1, except that one of the raw materials was equimolar N-Boc-4-hydroxypiperidine, in replacement of 1-Boc-3-azetidinemethanol in the preparation method of compound (1-1). NMR test results of the compound 3 were as follows:

$^1$H NMR (400 MHz, $CDCl_3$) δ 8.38 (s, 1H), 6.80 (d, J=2.2 Hz, 2H), 6.67-6.51 (m, 2H), 6.31 (dd, J=16.8, 1.8 Hz, 1H), 5.84-5.63 (m, 3H), 5.05 (tt, J=11.3, 4.2 Hz, 1H), 4.85 (d, J=13.4 Hz, 1H), 4.20 (d, J=13.9 Hz, 1H), 3.86 (s, 6H), 3.33 (t, J=12.7 Hz, 1H), 3.02-2.85 (m, 1H), 2.34 (t, J=11.8 Hz, 2H), 2.11 (d, J=13.0 Hz, 2H). $^{13}$C NMR (101 MHz, $CDCl_3$) δ 161.5, 157.8, 155.8, 154.7, 154.3, 144.1, 135.1, 132.1, 131.6, 106.3, 101.1, 100.0, 98.3, 79.6, 55.7, 55.6, 52.9, 45.5, 29.7, 28.4, 26.8. HRMS (ESI) calculated for $C_{21}H_{24}N_6NaO_3^+$: 431.1802, found 431.1805.

Example 4: Preparation of Compound 4 compound 4

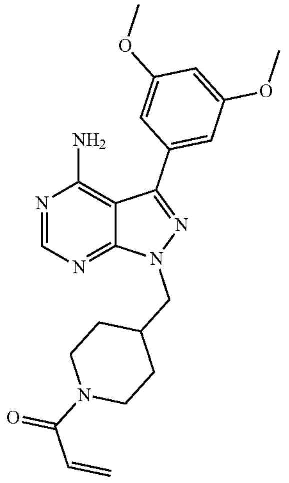

A specific preparation method was the same as the preparation method of compound 1, except that one of the raw materials was equimolar N-Boc-4-piperidinemethanol, in replacement of 1-Boc-3-azetidinemethanol in the preparation method of compound (1-1). NMR test results of the compound 4 were as follows:

$^1$H NMR (400 MHz, $CDCl_3$) δ 8.34 (s, 1H), 6.80 (d, J=2.3 Hz, 2H), 6.57-6.49 (m, 2H), 6.23 (d, J=16.8 Hz, 1H), 5.89 (s, 2H), 5.64 (d, J=10.6 Hz, 1H), 4.65 (d, J=13.3 Hz, 1H), 4.33 (d, J=7.1 Hz, 2H), 3.97 (d, J=13.8 Hz, 1H), 3.85 (s, 6H), 3.00 (t, J=12.9 Hz, 1H), 2.62 (t, J=12.9 Hz, 1H), 2.33 (d, J=11.0 Hz, 1H), 1.66 (d, J=16.3 Hz, 3H), 1.33 (td, J=14.3, 7.5 Hz, 2H). $^{13}$C NMR (100 MHz, $CDCl_3$) δ 165.4, 161.5, 161.5, 157.9, 156.0, 154.7, 144.3, 134.9, 127.9, 127.9, 127.4, 106.4, 101.1, 99.9, 98.2, 55.6, 51.9, 45.6, 41.8, 36.8, 30.5, 29.4. HRMS (ESI) calculated for $C_{22}H_{26}N_6NaO_3^+$: 445.1959, found 445.1961.

Example 5: Preparation of Compound 5 compound 5

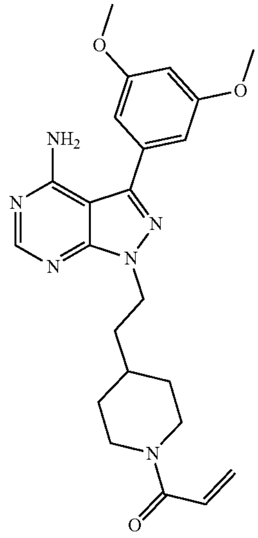

A specific preparation method was the same as the preparation method of compound 1, except that one of the raw materials was equimolar N-Boc-4-piperidineethanol, in replacement of 1-Boc-3-azetidinemethanol in the preparation method of compound (1-1). NMR test results of the compound 5 were as follows:

$^1$H NMR (400 MHz, $CDCl_3$) δ 8.38 (d, J=1.1 Hz, 1H), 6.81 (d, J=2.3 Hz, 2H), 6.57 (d, J=2.4 Hz, 1H), 6.44-6.36 (m, 2H), 5.68 (dd, J=9.6, 2.7 Hz, 1H), 4.50 (dd, J=12.8, 6.9 Hz, 2H), 3.87 (s, 7H), 3.80-3.72 (m, 2H), 3.72-3.65 (m, 1H), 3.57-3.47 (m, 2H), 3.01 (d, J=7.3 Hz, 1H), 1.65 (m, 4H). $^{13}$C NMR (100 MHz, $CDCl_3$) δ 166.3, 162.5, 158.7, 156.8, 155.2, 145.2, 136.0, 128.9, 128.4, 107.4, 102.1, 99.3, 56.6, 47.3, 45.6, 43.2, 36.9, 34.6, 33.5, 32.9, 32.6, 30.7, 30.4. HRMS (ESI) calculated for $C_{23}H_{28}N_6NaO_3^+$: 459.2115, found 459.2115.

Example 6: Preparation of Compound 6 compound 6

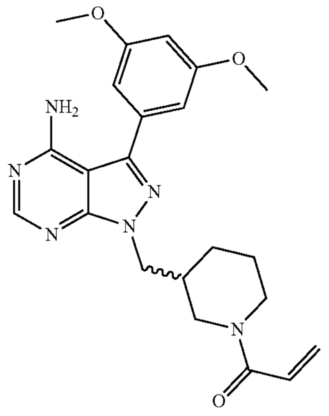

A specific preparation method was the same as the preparation method of compound 1, except that one of the raw materials was equimolar 1-Boc-3-hydroxymethylpiperidine, in replacement of 1-Boc-3-azetidinemethanol in the preparation method of compound (1-1). NMR test results of the compound 6 were as follows:

$^1$H NMR (400 MHz, $CDCl_3$) δ 8.39-8.33 (m, 1H), 6.93-6.75 (m, 2H), 6.63-6.46 (m, 2H), 6.21 (dd, J=16.9, 8.7 Hz, 1H), 5.99 (s, 2H), 5.61 (dd, J=32.0, 10.5 Hz, 1H), 4.53-4.27 (m, 3H), 3.86 (s, 6H), 3.07 (dt, J=23.7, 12.4 Hz, 1H), 2.81 (dt, J=44.0, 12.0 Hz, 1H), 2.35 (s, 1H), 1.93 (s, 1H), 1.58-1.29 (m, 2H), 1.26 (m, 2H). $^{13}$C NMR (100 MHz, $CDCl_3$) δ 165.5, 161.6, 157.9, 155.9, 154.7, 127.8, 127.4, 106.3, 101.3, 98.2, 55.6, 49.8, 49.7, 49.5, 46.5, 45.8, 42.7, 37.4, 36.4, 28.7, 25.2, 24.1. HRMS (ESI) calculated for $C_{22}H_{26}N_6NaO_3^+$: 445.1959, found 445.1961.

Example 7: Preparation of Compound 7 compound 7

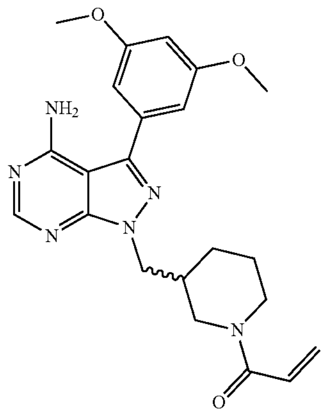

A specific preparation method was the same as the preparation method of compound 1, except that one of the raw materials was equimolar tert-Butyl 4-(2-hydroxyethyl)piperazine-1-carboxylate, in replacement of 1-Boc-3-azetidinemethanol in the preparation method of compound (1-1). NMR test results of the compound 7 were as follows:

$^1$H NMR (400 MHz, $CDCl_3$) δ 8.36 (s, 1H), 6.80 (d, J=2.3 Hz, 2H), 6.60-6.47 (m, 2H), 6.26 (dd, J=16.8, 1.9 Hz, 1H), 5.67 (dd, J=10.5, 1.9 Hz, 1H), 4.57 (t, J=6.7 Hz, 2H), 3.85 (s, 6H), 3.62 (s, 2H), 3.49 (s, 2H), 2.96 (t, J=6.7 Hz, 2H), 2.56 (t, J=5.0 Hz, 4H). $^{13}$C NMR (100 MHz, $CDCl_3$) δ 165.3, 161.5, 157.4, 155.1, 154.5, 144.6, 134.8, 127.9, 127.4, 106.3, 101.2, 98.2, 95.6, 56.7, 55.6, 52.6, 50.9, 45.6, 44.4, 41.8, 31.9, 29.1. HRMS (ESI) calculated for $C_{22}H_{27}N_7NaO_3^+$: 460.2068, found 460.2072.

Example 8: Preparation of Compound 8 compound 8

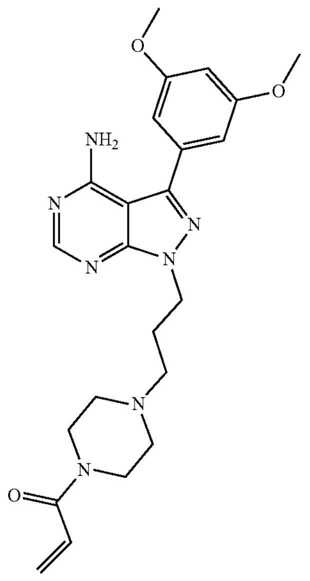

A specific preparation method was the same as the preparation method of compound 1, except that one of the raw materials was equimolar 1-Boc-4-(3-hydroxypropane)piperazine, in replacement of 1-Boc-3-azetidinemethanol in the preparation method of compound (1-1). NMR test results of the compound 8 were as follows:

$^1$H NMR (400 MHz, $CDCl_3$) δ 8.36 (s, 1H), 6.81 (d, J=2.3 Hz, 2H), 6.58-6.50 (m, 2H), 5.88 (s, 2H), 5.69 (dd, J=10.5, 1.9 Hz, 1H), 4.52 (t, J=6.9 Hz, 2H), 3.86 (s, 6H), 3.69 (d, J=6.9 Hz, 2H), 3.57 (s, 2H), 2.51 (dt, J=10.8, 6.0 Hz, 6H), 2.21 (p, J=7.0 Hz, 2H). $^{13}$C NMR (100 MHz, $CDCl_3$) δ 165.3, 160.3, 154.4, 133.4, 133.3, 132.2, 132.1, 132.0, 129.0, 128.6, 128.6, 128.4, 128.1, 127.3, 127.3, 107.9, 100.5, 55.4, 55.3, 53.1, 52.5, 45.2, 26.4. HRMS (ESI) calculated for $C_{23}H_{29}N_7NaO_3^+$: 474.2224, found 474.2226.

Example 9: Preparation of Compound 9 compound 9

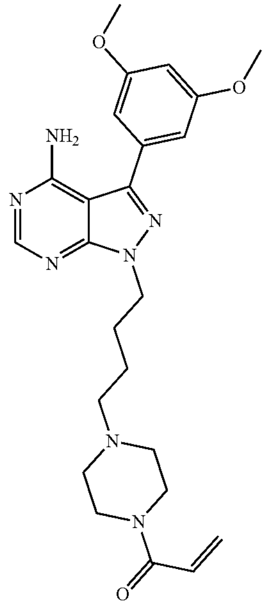

A specific preparation method was the same as the preparation method of compound 1, except that one of the raw materials was equimolar 1-Boc-4-(4-hydroxybutane)piperazine, in replacement of 1-Boc-3-azetidinemethanol in the preparation method of compound (1-1). NMR test results of the compound 9 were as follows:

$^1H$ NMR (400 MHz, $CDCl_3$) δ 8.40-8.36 (m, 1H), 6.81 (dd, J=3.2, 2.0 Hz, 2H), 6.54 (ddd, J=17.4, 8.7, 4.1 Hz, 2H), 6.28 (dt, J=16.9, 2.5 Hz, 1H), 5.72-5.66 (m, 1H), 5.61 (s, 2H), 4.46 (s, 2H), 3.89-3.82 (m, 6H), 3.67 (s, 2H), 3.54 (s, 2H), 2.41 (s, 6H), 2.01 (s, 2H), 1.56 (s, 2H). $^{13}C$ NMR (100 MHz, MeOD) δ 169.4, 166.0, 152.2, 151.70, 147.6, 145.9, 132.7, 128.5, 126.6, 106.2, 106.1, 101.5, 101.4, 96.5, 56.6, 54.7, 53.5, 51.1, 40.5, 39.1, 38.5, 35.2, 28.3, 22.7. HRMS (ESI) calculated for $C_{24}H_{31}N_7NaO_3^+$: 488.2381, found 488.2383.

Example 10: Preparation of Compound 10 compound 10

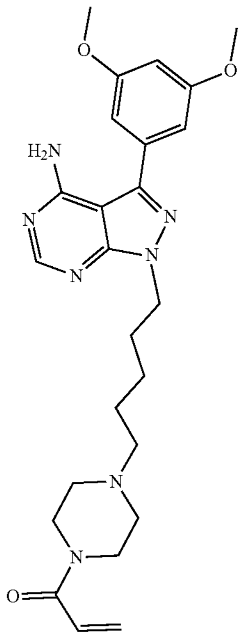

A specific preparation method was the same as the preparation method of compound 1, except that one of the raw materials was equimolar 1-Boc-4-(5-hydroxypentane)piperazine, in replacement of 1-Boc-3-azetidinemethanol in the preparation method of compound (1-1). NMR test results of the compound 10 were as follows:

$^1H$ NMR (400 MHz, $CDCl_3$) δ 8.38 (s, 1H), 6.82-6.80 (m, 2H), 6.58-6.55 (m, 1H), 6.53 (d, J=10.4 Hz, 1H), 6.27 (d, J=16.7 Hz, 1H), 5.68 (d, J=10.6 Hz, 1H), 5.61 (s, 2H), 4.43 (s, 2H), 3.86 (s, 6H), 3.67 (s, 2H), 3.53 (s, 2H), 2.42-2.38 (m, 4H), 2.34-2.30 (m, 2H), 2.02-1.96 (m, 2H), 1.54 (d, J=7.4 Hz, 2H), 1.39 (d, J=6.9 Hz, 2H). $^{13}C$ NMR (100 MHz, $CDCl_3$) δ 165.3, 161.6, 157.7, 155.9, 154.3, 144.0, 135.1, 127.7, 127.5, 106.4, 101.1, 100.0, 98.3, 58.2, 55.6, 53.4, 52.7, 47.1, 45.7, 41.8, 40.5, 29.6, 29.3, 26.2, 24.5. HRMS (ESI) calculated for $C_{25}H_{33}N_7NaO_3^+$: 502.2537, found 502.2539.

Example 11: Preparation of Compound 11 compound 11

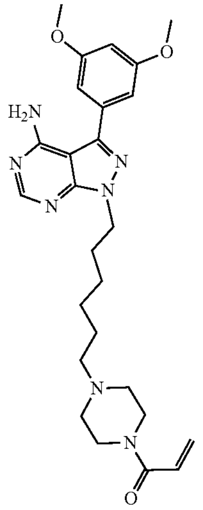

A specific preparation method was the same as the preparation method of compound 1, except that one of the raw materials was equimolar 1-Boc-4-(6-hydroxyhexane)piperazine, in replacement of 1-Boc-3-azetidinemethanol in the preparation method of compound (1-1). NMR test results of the compound 11 were as follows:

$^1$H NMR (400 MHz, $CDCl_3$) δ 8.34 (d, J=1.3 Hz, 1H), 6.81 (dd, J=2.3, 1.3 Hz, 2H), 6.61-6.52 (m, 2H), 6.29 (dt, J=16.9, 1.6 Hz, 1H), 6.00 (s, 2H), 5.69 (dt, J=10.5, 1.6 Hz, 1H), 4.43 (t, J=7.3 Hz, 2H), 3.86 (d, J=1.3 Hz, 6H), 3.69 (t, J=5.0 Hz, 2H), 3.56 (t, J=4.9 Hz, 2H), 2.42 (t, J=5.0 Hz, 4H), 2.33 (t, J=7.6 Hz, 2H), 1.97 (t, J=7.2 Hz, 2H), 1.54-1.45 (m, 2H), 1.38 (t, J=4.3 Hz, 4H). $^{13}$C NMR (100 MHz, $CDCl_3$) δ 165.3, 161.5, 157.8, 155.3, 154.1, 144.2, 135.0, 135.0, 127.9, 127.5, 127.5, 106.4, 106.4, 101.1, 98.2, 58.3, 55.6, 53.4, 52.7, 47.2, 45.7, 41.8, 29.7, 27.0, 26.6, 26.5. HRMS (ESI) calculated for $C_{26}H_{35}N_7NaO_3^+$: 516.2694, found 516.2696.

Example 12: Preparation of Compound 12 compound 12

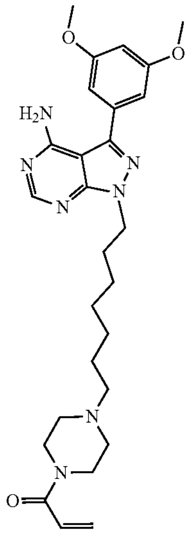

A specific preparation method was the same as the preparation method of compound 1, except that one of the raw materials was equimolar 1-Boc-4-(7-hydroxyheptane)piperazine, in replacement of 1-Boc-3-azetidinemethanol in the preparation method of compound (1-1). NMR test results of the compound 12 were as follows:

$^1$H NMR (400 MHz, $CDCl_3$) δ 8.38 (d, J=2.8 Hz, 1H), 6.82 (t, J=2.5 Hz, 2H), 6.62-6.50 (m, 2H), 6.33-6.23 (m, 1H), 5.77-5.56 (m, 3H), 4.42 (s, 2H), 3.86 (d, J=2.8 Hz, 6H), 3.70 (s, 2H), 3.57 (s, 2H), 2.50-2.37 (m, 4H), 2.33 (s, 2H), 1.96 (s, 2H), 1.47 (s, 2H), 1.33 (d, J=27.0 Hz, 6H). $^{13}$C NMR (101 MHz, $CDCl_3$) δ 165.6, 161.8, 158.1, 156.1, 154.5, 144.3 135.5, 135.5, 128.1, 127.8, 106.7, 101.4, 101.4, 98.6, 58.7, 55.9, 53.7, 53.1, 47.5, 46.0, 42.2, 30.0, 29.9, 29.3, 27.6, 26.9, 26.8. HRMS (ESI) calculated for $C_{27}H_{37}N_7NaO_3^+$: 530.2850, found 530.2852.

Example 13: Preparation of Compound 13 compound 13

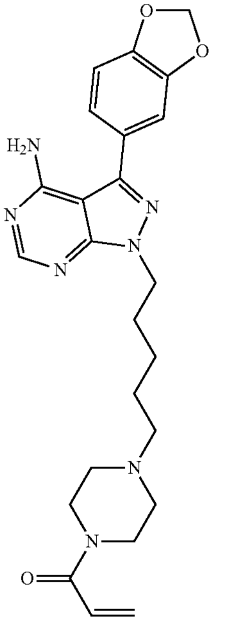

A specific preparation method was the same as the preparation method of compound 1, except that one of the raw materials was equimolar 3,4-methylenephenylboronic acid, in replacement of 3,5-dimethoxyphenylboronic acid in the preparation method of compound (1-2). NMR test results of the compound 13 were as follows:

$^1H$ NMR (400 MHz, $CDCl_3$) δ 8.36 (s, 1H), 7.16 (d, J=2.7 Hz, 1H), 6.97 (d, J=7.9 Hz, 1H), 6.62-6.49 (m, 1H), 6.28 (dd, J=16.9, 2.0 Hz, 1H), 6.06 (s, 2H), 5.86-5.65 (m, 3H), 4.42 (t, J=7.2 Hz, 2H), 3.70 (d, J=7.5 Hz, 2H), 3.55 (t, J=5.1 Hz, 2H), 2.43 (t, J=4.9 Hz, 4H), 2.35 (t, J=7.6 Hz, 2H), 1.99 (td, J=16.9, 15.0, 9.4 Hz, 2H), 1.79-1.14 (m, 6H). $^{13}C$ NMR (100 MHz, $CDCl_3$) δ 165.2, 157.8, 155.7, 154.2, 148.6, 148.5, 143.8, 127.4, 127.1, 122.1, 109.0, 108.9, 101.6, 101.5, 98.2, 58.1, 53.3, 52.7, 46.9, 45.6, 41.7, 29.5, 26.1, 24.5. HRMS (ESI) calculated for $C_{24}H_{29}N_7NaO_3^+$: 4860.2224, found 4860.2226.

Example 14: Preparation of Compound 14 compound 14

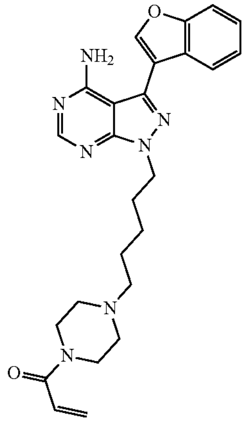

A specific preparation method was the same as the preparation method of compound 1, except that one of the raw materials was equimolar benzofuran-2-boronic acid, in replacement of 3,5-dimethoxyphenylboronic acid in the preparation method of compound (1-2). NMR test results of the compound 14 were as follows:

$^1H$ NMR (400 MHz, $CDCl_3$) δ 8.39 (s, 1H), 7.68 (dd, J=7.3, 1.5 Hz, 1H), 7.59-7.55 (m, 1H), 7.40-7.32 (m, 3H), 6.53 (dd, J=16.8, 10.6 Hz, 1H), 6.28 (dd, J=16.9, 1.9 Hz, 1H), 5.68 (dd, J=10.6, 2.0 Hz, 1H), 4.46 (t, J=7.2 Hz, 2H), 3.69 (s, 2H), 3.55 (s, 2H), 2.44 (s, 4H), 2.36 (t, J=7.6 Hz, 2H), 2.01 (p, J=7.4 Hz, 2H), 1.57 (q, J=7.6 Hz, 2H), 1.44-1.36 (m, 2H). $^{13}C$ NMR (100 MHz, $CDCl_3$) δ 165.3, 163.8, 157.6, 156.0 154.4, 149.5, 134.7, 128.3, 127.8, 127.4, 125.1, 124.0, 121.7, 111.0, 104.3, 97.9, 58.1, 53.3, 52.7, 47.3, 45.6, 41.7, 29.5, 26.1, 24.4. HRMS (ESI) calculated for $C_{25}H_{29}N_7NaO_2^+$: 482.2269, found 482.2271.

Example 15: Preparation of Compound 15 compound 15

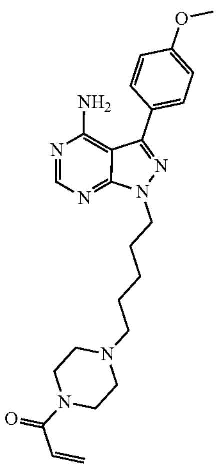

A specific preparation method was the same as the preparation method of compound 1, except that one of the raw materials was equimolar p-methoxyboronic acid, in replacement of 3,5-dimethoxyphenylboronic acid in the preparation method of compound (1-2). NMR test results of the compound 15 were as follows:

$^1H$ NMR (400 MHz, MeOD) δ 8.24 (s, 1H), 7.61 (d, J=8.6 Hz, 2H), 7.18-7.06 (m, 2H), 6.82-6.64 (m, 1H), 6.19 (dd, J=16.7, 2.0 Hz, 1H), 5.74 (dd, J=10.6, 1.9 Hz, 1H), 4.41 (t, J=6.8 Hz, 2H), 3.88 (s, 3H), 3.62 (s, 4H), 2.48 (s, 4H), 2.39 (s, 2H), 1.96 (q, J=7.3 Hz, 2H), 1.60-1.52 (m, 2H), 1.35 (q, J=7.9 Hz, 2H). $^{13}C$ NMR (100 MHz, $CDCl_3$) δ 165.3, 157.7, 155.9, 155.9, 154.4, 143.6, 140.4, 133.9, 132.5, 129.6, 127.8, 126.7, 125.9, 124.7, 64.1, 58.2, 53.4, 52.7, 48.6, 47.1, 29.5, 26.0, 24.5, 15.5. HRMS (ESI) calculated for $C_{24}H_{31}N_7NaO_2^+$: 472.2426, found 472.2428.

Example 16: Preparation of Compound 16 compound 16

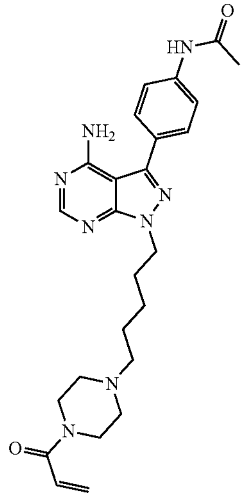

A specific preparation method was the same as the preparation method of compound 1, except that one of the raw materials was equimolar 4-acetylaminophenylboronic acid, in replacement of 3,5-dimethoxyphenylboronic acid in the preparation method of compound (1-2). NMR test results of the compound 16 were as follows:

$^1$H NMR (400 MHz, $CDCl_3$) δ 8.24 (d, J=1.3 Hz, 1H), 8.01 (s, 1H), 7.54-7.43 (m, 3H), 6.72 (dd, J=16.9, 10.7 Hz, 1H), 6.18 (dt, J=16.8, 1.7 Hz, 1H), 5.73 (dt, J=10.6, 1.7 Hz, 1H), 4.43 (t, J=6.7 Hz, 2H), 3.60 (q, J=6.7, 4.6 Hz, 4H), 2.46 (d, J=5.2 Hz, 4H), 2.37 (t, J=7.6 Hz, 2H), 2.16 (d, J=1.4 Hz, 3H), 1.97 (t, J=7.4 Hz, 2H), 1.57 (dd, J=11.0, 4.7 Hz, 2H), 1.34 (p, J=7.6 Hz, 2H). $^{13}$C NMR (100 MHz, MeOD) δ 170.6, 165.9, 158.4, 155.4, 153.8, 144.4, 139.14, 133.2, 129.6, 127.3, 127.3, 123.7, 120.4, 120.1, 100.0, 97.6, 57.6, 52.8, 52.3, 45.0, 41.3, 28.9, 25.3, 23.9, 22.4. HRMS (ESI) calculated for $C_{25}H_{32}N_8NaO_2^+$: 472.2426, found 472.2428.

Example 17: Preparation of Compound 17 compound 17

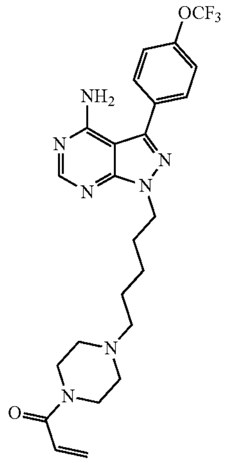

A specific preparation method was the same as the preparation method of compound 1, except that equimolar 4-trifluoromethoxyphenylboronic acid, in replacement of 3,5-dimethoxyphenylboronic acid in the preparation method of compound (1-2). NMR test results of the compound 17 were as follows:

$^1$H NMR (400 MHz, $CDCl_3$) δ 8.27 (s, 1H), 7.70 (t, J=7.6 Hz, 1H), 7.63 (d, J=10.6 Hz, 1H), 7.49-7.42 (m, 1H), 7.35 (dd, J=7.8, 5.3 Hz, 1H), 6.73 (dd, J=16.8, 10.7 Hz, 1H), 6.18 (dd, J=16.8, 1.9 Hz, 1H), 5.73 (dd, J=10.7, 2.0 Hz, 1H), 4.44 (t, J=6.8 Hz, 2H), 3.61 (d, J=5.4 Hz, 4H), 2.50-2.37 (m, 4H), 2.35 (d, J=7.7 Hz, 2H), 1.99 (q, J=7.1 Hz, 2H), 1.59-1.55 (m, 2H), 1.35 (s, 2H). $^{13}$C NMR (100 MHz, $CDCl_3$) δ 166.2, 158.5, 156.8, 155.4, 150.6, 143.3, 136.3, 131.8, 128.6, 128.4, 127.6, 122.3, 121.9, 120.1, 99.2, 59.1, 54.3, 53.6, 48.1, 46.6, 42.8, 30.4, 27.1, 25.4. HRMS (ESI) calculated for $C_{24}H_{28}F_3N_7NaO_2^+$: 526.2143, found 526.2145.

Example 18: Preparation of Compound 18 compound 18

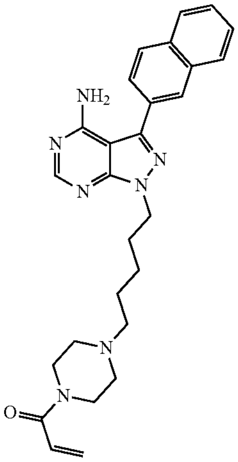

A specific preparation method was the same as the preparation method of compound 1, except that one of the raw materials was equimolar 2-naphthaleneboronic acid in replacement of 3,5-dimethoxyphenylboronic acid in the preparation method of compound (1-2). NMR test results of the compound 18 were as follows:

$^1$H NMR (400 MHz, $CDCl_3$) δ 8.41 (s, 1H), 8.17 (s, 1H), 8.03 (d, J=8.4 Hz, 1H), 7.93 (dd, J=9.3, 3.6 Hz, 2H), 7.82 (d, J=8.4 Hz, 1H), 7.58 (dd, J=6.2, 3.2 Hz, 2H), 6.51 (dd, J=16.8, 10.5 Hz, 1H), 6.27 (d, J=16.8 Hz, 1H), 5.67 (d, J=10.7 Hz, 1H), 4.49 (t, J=7.2 Hz, 2H), 3.68 (s, 2H), 3.51 (d, J=15.2 Hz, 2H), 2.37 (dd, J=19.5, 12.3 Hz, 6H), 2.04 (dd, J=14.6, 7.4 Hz, 2H), 1.57 (dd, J=14.7, 7.5 Hz, 2H), 1.42 (dd, J=14.9, 7.9 Hz, 2H). $^{13}$C NMR (100 MHz, $CDCl_3$) δ 165.28, 157.63, 155.97, 154.54, 149.88, 142.42, 135.37, 135.35, 130.91, 127.75, 127.50, 127.24, 126.68, 121.64, 121.38, 121.00, 118.73, 98.31, 58.16, 53.43, 52.73, 47.17, 45.72, 41.87, 29.53, 26.24, 24.52. HRMS (ESI) calculated for $C_{27}H_{31}N_7NaO$+: 492.2482, found 492.2484.

Example 19: Preparation of Compound 19 compound 19

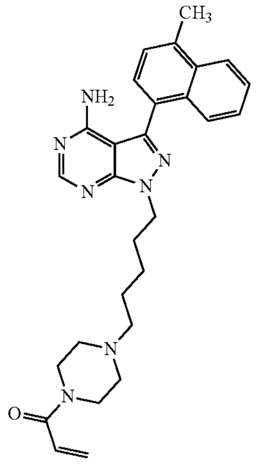

A specific preparation method was the same as the preparation method of compound 1, except that one of the raw materials was equimolar 4-methylnaphthaleneboronic acid, in replacement of 3,5-dimethoxyphenylboronic acid in the preparation method of compound (1-2). NMR test results of the compound 19 were as follows:

$^1$H NMR (400 MHz, $CDCl_3$) δ 8.37 (s, 1H), 8.10 (d, J=8.4 Hz, 1H), 7.91 (d, J=8.3 Hz, 1H), 7.63-7.41 (m, 4H), 6.52 (dd, J=16.8, 10.5 Hz, 1H), 6.26 (dd, J=16.8, 1.7 Hz, 1H), 5.67 (dd, J=10.5, 1.7 Hz, 1H), 4.50 (t, J=7.1 Hz, 2H), 3.66 (s, 2H), 3.49 (d, J=16.9 Hz, 2H), 2.78 (s, 3H), 2.36 (dd, J=19.3, 12.0 Hz, 6H), 2.13-1.98 (m, 2H), 1.57 (dt, J=14.9, 7.6 Hz, 2H), 1.42 (dt, J=15.0, 7.6 Hz, 2H). $^{13}$C NMR (100 MHz, $CDCl_3$) δ 165.27, 159.72, 157.75, 155.67, 154.23, 144.16, 134.49, 130.52, 127.93, 127.88, 127.43, 120.40, 120.11, 115.46, 114.30, 98.54, 98.31, 63.68, 58.15, 53.31, 52.69, 47.03, 41.74, 29.71, 29.54, 26.11, 24.50, 24.04. HRMS (ESI) calculated for $C_{28}H_{33}N_7NaO+$: 570.1587, found 570.1590.

Example 20: Preparation of Compound 20 compound 20

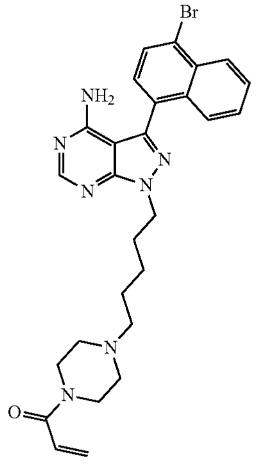

A specific preparation method was the same as the preparation method of compound 1, except that one of the raw materials was equimolar 4-bromonaphthaleneboronic acid, in replacement of 3,5-dimethoxyphenylboronic acid in the preparation method of compound (1-2). NMR test results of the compound 20 were as follows:

$^1$H NMR (400 MHz, $CDCl_3$) δ 8.38 (s, 1H), 8.11 (d, J=8.4 Hz, 1H), 7.92 (d, J=8.3 Hz, 1H), 7.64-7.42 (m, 4H), 6.53 (dd, J=16.8, 10.5 Hz, 1H), 6.27 (dd, J=16.8, 1.7 Hz, 1H), 5.68 (dd, J=10.5, 1.7 Hz, 1H), 4.51 (t, J=7.1 Hz, 2H), 3.67 (s, 2H), 3.50 (d, J=17.0 Hz, 2H), 2.37 (dd, J=19.3, 12.0 Hz, 6H), 2.13-1.99 (m, 2H), 1.58 (dt, J=14.9, 7.6 Hz, 2H), 1.43 (dt, J=15.0, 7.6 Hz, 2H). $^{13}$C NMR (100 MHz, $CDCl_3$) δ 165.16, 157.62, 157.55, 155.88, 154.26, 149.40, 134.60, 128.22, 127.80, 127.72, 127.32, 125.04, 123.91, 121.64, 121.60, 110.91, 104.17, 99.87, 97.77, 58.01, 53.21, 52.59, 47.20, 45.47, 41.63, 29.34, 24.31. HRMS (ESI) calculated for $C_{27}H_{30}BrN_7NaO+$: 570.1587, found 570.1590.

Example 21: Preparation of Compound 21 compound 21

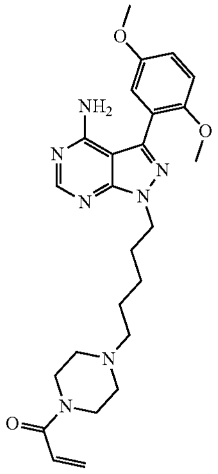

A specific preparation method was the same as the preparation method of compound 1, except that one of the raw materials was equimolar 2,5-dimethoxyphenylboronic acid, in replacement of 3,5-dimethoxyphenylboronic acid in the preparation method of compound (1-2). NMR test results of the compound 21 were as follows:

$^1$H NMR (400 MHz, $CDCl_3$) δ 8.35 (s, 1H), 7.07 (s, 1H), 7.02 (d, J=8.6 Hz, 2H), 6.56 (dd, J=16.8, 10.6 Hz, 1H), 6.28 (d, J=16.8 Hz, 1H), 5.70 (d, J=7.6 Hz, 1H), 4.44 (t, J=7.1 Hz, 2H), 3.81 (d, J=11.0 Hz, 6H), 3.69 (s, 2H), 3.55 (s, 2H), 2.47-2.32 (m, 6H), 2.03 (dd, J=14.0, 7.0 Hz, 2H), 1.61-1.52 (m, 2H), 1.41 (dd, J=14.7, 7.6 Hz, 2H). $^{13}$C NMR (100 MHz, $CDCl_3$) δ 165.28, 158.41, 155.55, 154.40, 153.90, 150.49, 140.79, 127.83, 127.47, 123.11, 117.10, 116.10, 113.43, 100.37, 58.17, 56.76, 55.85, 53.35, 52.72, 47.06, 45.66, 41.80, 29.55, 26.21. HRMS (ESI) calculated for $C_{25}H_{33}N_7NaO_3^+$: 502.2537, found 502.2539.

Example 22: Preparation of Compound 22 compound 22

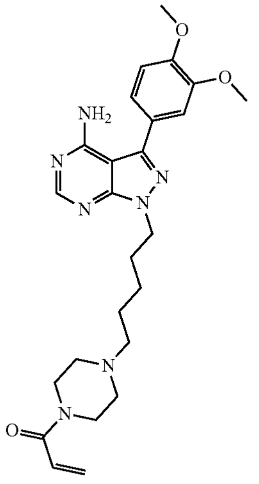

A specific preparation method was the same as the preparation method of compound 1, except that one of the raw materials was equimolar 3,4-dimethoxyphenylboronic acid, in replacement of 3,5-dimethoxyphenylboronic acid in the preparation method of compound (1-2). NMR test results of the compound 22 were as follows:

$^{1}H$ NMR (400 MHz, $CDCl_3$) δ 8.39 (s, 1H), 7.27 (s, 1H), 6.89 (s, 2H), 6.64-6.50 (m, 1H), 6.29 (d, J=16.6 Hz, 1H), 5.70 (d, J=10.2 Hz, 3H), 4.43 (d, J=6.9 Hz, 2H), 3.94 (s, 3H), 3.91 (s, 3H), 3.69 (s, 2H), 3.56 (s, 2H), 2.38 (dd, J=22.3, 15.1 Hz, 6H), 2.03-1.98 (m, 2H), 1.57 (d, J=6.9 Hz, 2H), 1.40 (d, J=7.0 Hz, 2H). $^{13}C$ NMR (100 MHz, $CDCl_3$) δ 165.34, 165.29, 157.82, 155.94, 155.91, 155.87, 154.22, 154.05, 153.99, 144.18, 138.75, 128.59, 127.92, 127.42, 105.53, 98.33, 61.03, 58.18, 56.33, 53.39, 52.70, 47.06, 29.61, 26.19, 24.53. HRMS (ESI) calculated for $C_{25}H_{33}N_7NaO_3^+$: 502.2537, found 502.2539.

Example 23: Preparation of Compound 23 compound 23

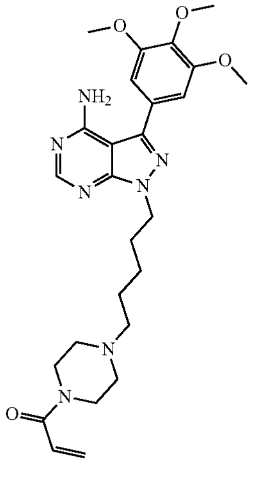

A specific preparation method was the same as the preparation method of compound 1, except that one of the raw materials was equimolar 3,4,5-trimethoxyphenylboronic acid, in replacement of 3,5-dimethoxyphenylboronic acid in the preparation method of compound (1-2). NMR test results of the compound 23 were as follows:

$^{1}H$ NMR (400 MHz, $CDCl_3$) δ 8.30 (s, 1H), 6.82 (d, J=1.3 Hz, 2H), 6.47 (ddd, J=16.8, 10.5, 1.3 Hz, 1H), 6.19 (dt, J=16.8, 1.6 Hz, 1H), 5.87 (s, 2H), 5.60 (dt, J=10.5, 1.6 Hz, 1H), 4.36 (t, J=7.3 Hz, 2H), 3.86 (d, J=1.3 Hz, 6H), 3.83 (d, J=1.3 Hz, 3H), 3.60 (t, J=5.0 Hz, 2H), 3.47 (t, J=5.0 Hz, 2H), 2.33 (t, J=5.1 Hz, 4H), 2.27 (d, J=7.5 Hz, 2H), 1.93 (q, J=7.6 Hz, 2H), 1.49 (t, J=7.6 Hz, 2H), 1.33 (d, J=7.6 Hz, 2H). $^{13}C$ NMR (100 MHz, $CDCl_3$) δ 165.2, 158.0, 155.8, 154.2, 153.9, 144.1, 138.8, 128.6, 128.6, 128.4, 127.7, 127.5, 105.6, 98.3, 61.0, 58.2, 56.3, 53.4, 52.7, 47.0, 45.7, 41.9, 29.7, 29.6, 26.3, 24.5. HRMS (ESI) calculated for $C_{26}H_{35}N_7NaO_4^+$: 532.2643, found 536.2645.

Example 24: Preparation of Compound 24 compound 24

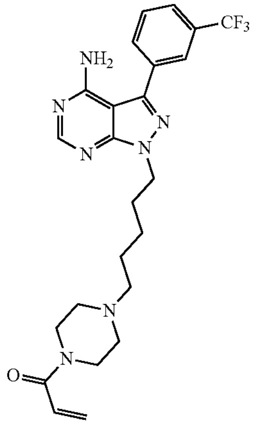

A specific preparation method was the same as the preparation method of compound 1, except that one of the raw materials was equimolar 3-trifluoromethylphenylboronic acid, in replacement of 3,5-dimethoxyphenylboronic acid in the preparation method of compound (1-2). NMR test results of the compound 24 were as follows:

$^{1}H$ NMR (400 MHz, $CDCl_3$) δ 8.37 (s, 1H), 7.68-7.54 (m, 3H), 7.33 (d, J=6.5 Hz, 1H), 6.59-6.47 (m, 1H), 6.25 (dd, J=16.8, 4.6 Hz, 1H), 5.95-5.59 (m, 3H), 4.43 (d, J=6.6 Hz, 2H), 3.64 (d, J=9.2 Hz, 2H), 3.52 (s, 2H), 2.39 (d, J=5.7 Hz, 4H), 2.32 (d, J=7.3 Hz, 2H), 1.98 (q, J=7.1 Hz, 2H), 1.56 (s, 2H), 1.42-1.32 (m, 2H). $^{13}C$ NMR (100 MHz, $CDCl_3$) δ 165.3, 157.7, 155.8, 154.5, 149.8, 142.5, 135.3, 130.9, 127.7, 127.5, 126.7, 121.4, 121.0, 98.3, 58.1, 53.4, 52.7, 47.2, 45.7, 41.9, 29.7, 29.5, 26.2, 24.5. HRMS (ESI) calculated for $C_{24}H_{28}F_3N_7NaO^+$: 510.2205, found 510.2207.

Example 25: Preparation of Compound 25 compound 25

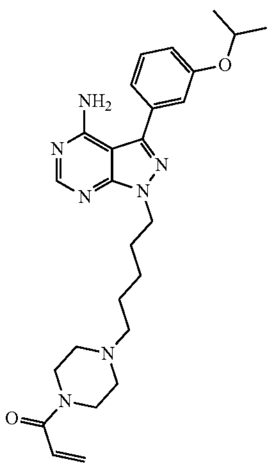

A specific preparation method was the same as the preparation method of compound 1, except that one of the raw materials was equimolar 3-isopropoxyphenylboronic acid, in replacement of 3,5-dimethoxyphenylboronic acid in the preparation method of compound (1-2). NMR test results of the compound 25 were as follows:

$^{1}$H NMR (400 MHz, $CDCl_3$) δ 8.15 (d, J=1.2 Hz, 1H), 7.36 (t, J=7.9 Hz, 1H), 7.11 (dd, J=8.2, 5.0 Hz, 2H), 7.00-6.95 (m, 1H), 6.70-6.60 (m, 1H), 6.09 (dt, J=16.8, 1.6 Hz, 1H), 5.64 (dt, J=10.6, 1.6 Hz, 1H), 4.60 (q, J=6.0 Hz, 1H), 4.32 (t, J=6.8 Hz, 2H), 3.53 (t, J=6.3 Hz, 4H), 2.38 (s, 4H), 2.30 (t, J=7.6 Hz, 2H), 1.87 (d, J=7.1 Hz, 2H), 1.48 (t, J=7.8 Hz, 2H), 1.25 (dd, J=6.0, 1.3 Hz, 6H), 1.22 (d, J=7.4 Hz, 2H). $^{13}$C NMR (100 MHz, MeOD) δ 166.0, 158.6, 158.5, 155.4, 153.7, 144.7, 134.0, 130.2, 127.3, 127.3, 120.1, 116.4, 115.5, 100.0, 97.6, 69.9, 57.6, 52.8, 52.3, 46.4, 45.0, 41.3, 28.9, 25.2, 23.9, 21.0. HRMS (ESI) calculated for $C_{26}H_{35}N_7NaO_2^+$: 500.2744, found 500.2747.

Example 26: Preparation of Compound 26 compound 26

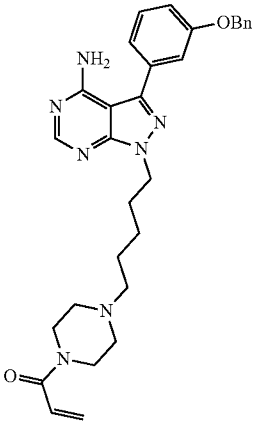

A specific preparation method was the same as the preparation method of compound 1, except that one of the raw materials was equimolar 3-benzyloxyphenylboronic acid, in replacement of 3,5-dimethoxyphenylboronic acid in the preparation method of compound (1-2). NMR test results of the compound 26 were as follows:

$^{1}$H NMR (400 MHz, $CDCl_3$) δ 8.37 (s, 1H), 7.49-7.27 (m, 8H), 7.11 (d, J=8.5 Hz, 1H), 6.54 (dd, J=16.8, 10.4 Hz, 1H), 6.28 (d, J=16.8 Hz, 1H), 5.69 (d, J=10.4 Hz, 1H), 5.43 (s, 2H), 5.17 (s, 2H), 4.44 (t, J=7.4 Hz, 2H), 3.62 (d, J=49.9 Hz, 4H), 2.39 (d, J=27.3 Hz, 6H), 2.03-1.93 (m, 2H), 1.38 (s, 2H). $^{13}$C NMR (100 MHz, $CDCl_3$) δ 165.3, 159.4, 157.7, 155.4, 154.2, 144.1, 136.6, 134.5, 133.3, 130.6, 128.7, 128.1, 127.7, 127.5, 127.4, 120.9, 116.0, 114.5, 98.2, 70.0, 58.1, 53.3, 52.7, 47.1, 45.7, 41.8, 29.5, 26.2, 24.5, 21.2. HRMS (ESI) calculated for $C_{30}H_{35}N_7NaO_2^+$: 548.2744, found 548.2747.

Example 27: Preparation of Compound 27 compound 27

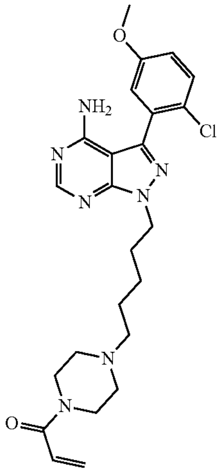

A specific preparation method was the same as the preparation method of compound 1, except that one of the raw materials was equimolar 2-chloro-5-methoxyphenylboronic acid, in replacement of 3,5-dimethoxyphenylboronic acid in the preparation method of compound (1-2). NMR test results of the compound 27 were as follows:

$^{1}$H NMR (400 MHz, $CDCl_3$) δ 8.35 (d, J=4.2 Hz, 1H), 7.43 (s, 1H), 6.99 (dq, J=19.8, 3.2 Hz, 2H), 6.53 (ddd, J=15.6, 10.7, 3.9 Hz, 1H), 6.25 (dd, J=16.9, 3.9 Hz, 1H), 5.80-5.22 (m, 3H), 4.45 (t, J=6.5 Hz, 2H), 3.82 (d, J=4.9 Hz, 3H), 3.68-3.63 (m, 2H), 3.51 (s, 2H), 2.39 (d, J=5.4 Hz, 4H), 2.31 (q, J=6.2, 5.4 Hz, 2H), 1.99 (q, J=6.8 Hz, 2H), 1.53 (q, J=7.1 Hz, 2H), 1.42-1.28 (m, 2H). $^{13}$C NMR (100 MHz, $CDCl_3$) δ 165.3, 158.6, 157.7, 155.9, 153.8, 141.1, 132.6, 131.1, 127.7, 127.5, 124.7, 116.9, 99.9, 70.5, 58.2, 55.7, 53.4, 52.7, 47.1, 45.7, 41.9, 29.5, 26.2, 24.5. HRMS (ESI) calculated for $C_{24}H_{30}ClN_7NaO_2^+$: 506.2042, found 506.2044.

Example 28: Preparation of Compound 28 compound 28

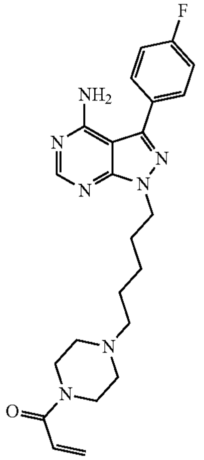

A specific preparation method was the same as the preparation method of compound 1, except that one of the raw materials was equimolar p-fluorophenylboronic acid, in replacement of 3,5-dimethoxyphenylboronic acid in the preparation method of compound (1-2). NMR test results of the compound 28 were as follows:

$^{1}H$ NMR (400 MHz, $CDCl_3$) δ 8.31 (s, 1H), 7.25 (s, 2H), 6.54 (dd, J=16.8, 10.5 Hz, 1H), 6.29 (dd, J=16.8, 1.7 Hz, 1H), 6.24 (s, 2H), 5.70 (d, J=10.5 Hz, 1H), 4.35 (t, J=7.0 Hz, 2H), 3.69 (t, J=29.6 Hz, 4H), 2.44 (d, J=31.0 Hz, 6H), 1.92 (dd, J=14.9, 7.4 Hz, 2H), 1.58 (s, 2H), 1.35-1.30 (m, 2H). $^{13}C$ NMR (100 MHz, $CDCl_3$) δ 165.21, 158.54, 157.68, 155.61, 153.68, 141.11, 132.50, 131.04, 127.66, 127.44, 124.68, 116.84, 99.80, 58.07, 55.65, 53.26, 52.63, 47.07, 45.59, 41.74, 29.40, 26.09, 24.40. HRMS (ESI) calculated for $C_{23}H_{28}FN_7NaO^+$: 460.2232, found 460.2230.

Example 29: Preparation of Compound 29 compound 29

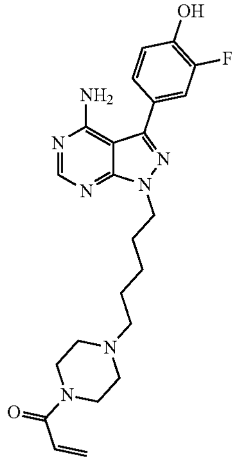

A specific preparation method was the same as the preparation method of compound 1, except that one of the raw materials was equimolar 3-fluoro-4-hydroxyphenylboronic acid, in replacement of 3,5-dimethoxyphenylboronic acid in the preparation method of compound (1-2). NMR test results of the compound 29 were as follows:

$^{1}H$ NMR (400 MHz, $CDCl_3$) δ 8.34 (s, 1H), 7.72-7.62 (m, 2H), 7.26-7.23 (m, 1H), 6.55 (dd, J=16.8, 10.5 Hz, 1H), 6.28 (dd, J=16.8, 1.9 Hz, 1H), 5.69 (dd, J=10.5, 1.9 Hz, 1H), 4.44 (t, J=7.2 Hz, 2H), 3.68 (s, 2H), 3.51 (d, J=21.5 Hz, 2H), 2.47-2.39 (m, 4H), 2.36-2.31 (m, 2H), 1.99 (dt, J=15.0, 7.5 Hz, 2H), 1.55 (dd, J=15.1, 7.6 Hz, 2H), 1.42-1.33 (m, 2H). $^{13}C$ NMR (100 MHz, $CDCl_3$) δ 165.30, 162.94, 161.55, 157.73, 157.26, 156.54, 154.10, 119.85, 117.25, 100.41, 100.29, 99.99, 61.49, 57.97, 53.20, 52.53, 47.28, 29.69, 29.65, 29.40, 29.26, 24.72, 24.24. HRMS (ESI) calculated for $C_{23}H_{28}FN_7NaO_2$+: 476.2181, found 476.2180.

Example 30: Preparation of Compound 30 compound 30

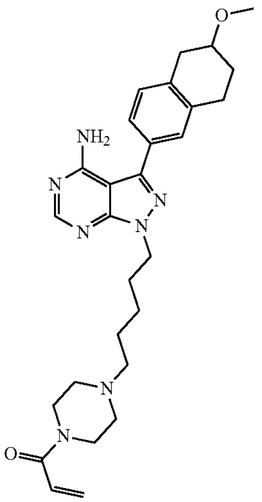

A specific preparation method was the same as the preparation method of compound 1, except that one of the raw materials was equimolar 6-methoxynaphthalene-2-boronic acid, in replacement of 3,5-dimethoxyphenylboronic acid in the preparation method of compound (1-2). NMR test results of the compound 30 were as follows:

$^{1}H$ NMR (400 MHz, $CDCl_3$) δ 8.37 (d, J=5.6 Hz, 1H), 8.08 (s, 1H), 7.91 (d, J=8.4 Hz, 1H), 7.83 (d, J=8.9 Hz, 1H), 7.77 (dd, J=8.4, 1.6 Hz, 1H), 7.26-7.19 (m, 2H), 6.51 (dd, J=16.8, 10.5 Hz, 1H), 6.31-6.16 (m, 1H), 5.77 (d, J=66.8 Hz, 2H), 5.67 (dd, J=10.5, 1.9 Hz, 1H), 4.47 (t, J=7.2 Hz, 2H), 3.97 (s, 3H), 3.69 (s, 2H), 3.54 (s, 2H), 2.38 (dd, J=21.6, 14.2 Hz, 6H), 2.02 (dt, J=14.8, 7.4 Hz, 2H), 1.63-1.53 (m, 2H), 1.41 (dt, J=15.1, 7.5 Hz, 2H). $^{13}C$ NMR (100 MHz, $CDCl_3$) δ 165.27, 158.50, 157.93, 155.54, 154.31, 144.47, 134.66, 129.73, 128.92, 128.23, 128.12, 127.81, 127.54, 127.43, 126.28, 119.94, 105.79, 98.49, 58.13, 55.42, 53.27, 52.70, 47.05, 45.55, 41.71, 29.57, 26.08, 24.51. HRMS (ESI) calculated for $C_{28}H_{33}N_7NaO_2^+$: 522.2588, found 522.2587.

Example 31: Preparation of Compound 31 compound 31

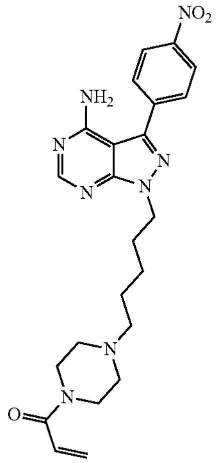

A specific preparation method was the same as the preparation method of compound 1, except that one of the raw materials was equimolar p-nitrophenylboronic acid, in replacement of 3,5-dimethoxyphenylboronic acid in the preparation method of compound (1-2). NMR test results of the compound 31 were as follows:

$^1$H NMR (400 MHz, $CDCl_3$) δ 8.45-8.36 (m, 3H), 7.92 (d, J=8.8 Hz, 2H), 6.54 (dd, J=16.8, 10.5 Hz, 1H), 6.27 (dd, J=16.9, 2.0 Hz, 1H), 5.90-5.63 (m, 3H), 4.48 (t, J=7.2 Hz, 2H), 3.67 (s, 2H), 3.59-3.50 (m, 2H), 2.42 (t, J=5.1 Hz, 4H), 2.35 (dd, J=8.5, 6.5 Hz, 2H), 2.01 (p, J=7.6 Hz, 2H), 1.63-1.55 (m, 2H), 1.41 (dt, J=11.4, 6.8 Hz, 2H). $^{13}$C NMR (100 MHz, $CDCl_3$) δ 165.3, 157.6, 155.9, 154.7, 148.0, 141.7, 139.6, 129.2, 127.8, 127.5, 124.6, 98.4, 77.2, 58.1, 53.4, 52.7, 47.4, 45.7, 41.8, 29.7, 29.5, 26.2, 24.5. HRMS (ESI) calculated for $C_{23}H_{28}N_8NaO_3^+$: 487.2177, found 487.2179.

Example 32: Preparation of Compound 32 compound 32

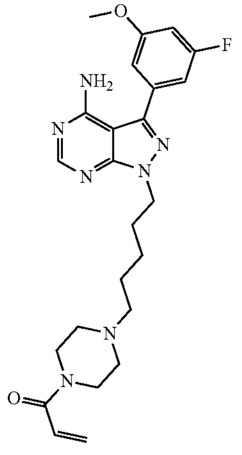

A specific preparation method was the same as the preparation method of compound 1, except that one of the raw materials was equimolar 3-fluoro-5-methoxyphenylboronic acid, in replacement of 3,5-dimethoxyphenylboronic acid in the preparation method of compound (1-2). NMR test results of the compound 31 were as follows:

$^1$H NMR (400 MHz, $CDCl_3$) δ 8.38 (s, 1H), 7.24 (d, J=2.1 Hz, 2H), 6.99-6.87 (m, 1H), 6.54 (dd, J=16.8, 10.6 Hz, 1H), 6.27 (dd, J=16.8, 1.9 Hz, 1H), 5.80-5.63 (m, 3H), 4.44 (t, J=7.2 Hz, 2H), 3.92 (s, 3H), 3.66 (d, J=12.5 Hz, 2H), 3.54 (s, 2H), 2.45-2.33 (m, 6H), 2.02-1.96 (m, 2H), 1.55 (dd, J=15.0, 7.5 Hz, 2H), 1.37 (dd, J=15.2, 7.2 Hz, 2H). $^{13}$C NMR (100 MHz, $CDCl_3$) δ 165.31, 164.85, 164.72, 162.35, 162.23, 157.51, 155.78, 154.50, 127.78, 127.48, 111.59, 111.33, 104.53, 104.28, 98.15, 58.13, 53.38, 52.69, 47.23, 45.66, 41.82, 29.49, 26.17, 24.51. HRMS (ESI) calculated for $C_{24}H_{30}FN_7NaO_2^+$: 490.2337, found 490.2335.

Example 33: Preparation of Compound 33 compound 33

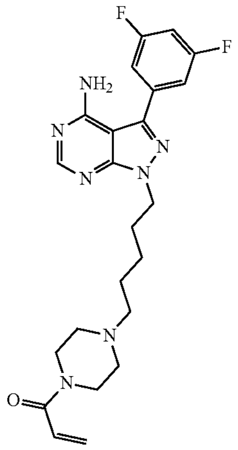

A specific preparation method was the same as the preparation method of compound 1, except that one of the raw materials was equimolar 3,5-difluorophenylboronic acid was used instead of 3,5-dimethoxyphenylboronic acid in the preparation method of compound (1-2). NMR test results of the compound 33 were as follows:

$^1$H NMR (400 MHz, $CDCl_3$) δ 8.36 (s, 1H), 7.01 (dd, J=8.4, 2.2 Hz, 2H), 6.73 (dt, J=10.5, 2.3 Hz, 1H), 6.55 (dd, J=16.8, 10.6 Hz, 1H), 6.28 (dd, J=16.8, 1.9 Hz, 1H), 5.83 (s, 2H), 5.69 (dd, J=10.5, 1.9 Hz, 1H), 4.44 (t, J=7.2 Hz, 2H), 3.66 (m, J=16.1 Hz, 2H), 3.55 (m, 2H), 2.37 (dd, J=23.0, 15.7 Hz, 6H), 1.98 (dd, J=14.9, 7.5 Hz, 2H), 1.56 (dd, J=14.8, 7.4 Hz, 2H), 1.45-1.36 (m, 2H). $^{13}$C NMR (100 MHz, $CDCl_3$) δ 165.28, 162.81, 161.77, 161.65, 157.58, 155.96, 154.41, 127.74, 127.49, 110.07, 110.04, 107.79, 107.57, 102.38, 102.13, 98.25, 58.15, 55.81, 53.35, 52.74, 47.12, 29.51, 24.50. HRMS (ESI) calculated for $C_{23}H_{27}F_2N_7NaO^+$: 478.2137, found 478.2139.

Example 34: Preparation of Compound 34 compound 34

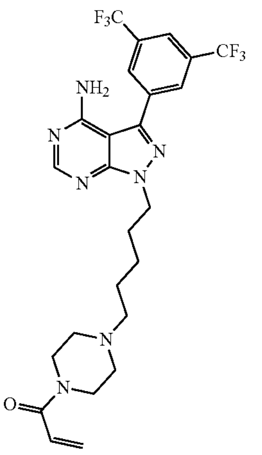

A specific preparation method was the same as the preparation method of compound 1, except that one of the raw materials was equimolar 3,5-bis(trifluoromethyl)phenylboronic acid, in replacement of 3,5-dimethoxyphenylboronic acid in the preparation method of compound (1-2). NMR test results of the compound 34 were as follows:

$^{1}$H NMR (400 MHz, $CDCl_3$) δ 8.44 (s, 1H), 8.20 (s, 2H), 7.99 (s, 1H), 6.61-6.51 (m, 1H), 6.28 (d, J=17.0 Hz, 1H), 5.69 (d, J=10.6 Hz, 1H), 4.48 (t, J=7.0 Hz, 2H), 3.64 (s, 4H), 2.39 (d, J=26.1 Hz, 6H), 2.05-1.99 (m, 2H), 1.78 (s, 2H), 1.38 (dd, J=23.0, 12.9 Hz, 2H). $^{13}$C NMR (100 MHz, $CDCl_3$) δ 165.3, 157.5, 156.0, 154.8, 140.9, 135.5, 133.2, 132.9, 132.6, 128.5, 127.8, 127.5, 124.4, 122.5, 121.7, 98.4, 58.1, 53.4, 52.7, 47.35 45.7, 41.8, 29.5, 26.2, 24.5. HRMS (ESI) calculated for $C_{25}H_{27}F_6N_7NaO^+$: 578.2073, found 578.2075.

Example 35: Preparation of Compound 35 compound 35

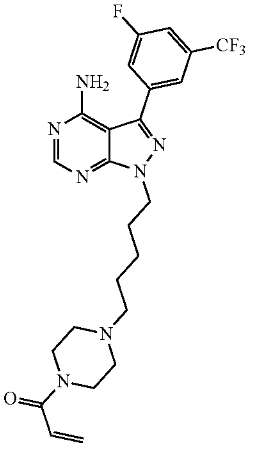

A specific preparation method was the same as the preparation method of compound 1, except that one of the raw materials was equimolar 3-fluoro-5-trifluoromethylphenylboronic acid, in replacement of 3,5-dimethoxyphenylboronic acid in the preparation method of compound (1-2). NMR test results of the compound 35 were as follows:

$^{1}$H NMR (400 MHz, $CDCl_3$) δ 8.35 (s, 1H), 7.73 (s, 1H), 7.58 (dd, J=8.7, 2.0 Hz, 1H), 7.40-7.37 (m, 1H), 6.48 (dd, J=16.8, 10.5 Hz, 1H), 6.20 (dd, J=16.8, 1.9 Hz, 1H), 5.61 (dd, J=10.5, 1.9 Hz, 1H), 4.39 (t, J=7.2 Hz, 2H), 3.60 (s, 2H), 3.47 (s, 2H), 2.34 (t, J=5.1 Hz, 4H), 2.30-2.24 (m, 2H), 1.96-1.90 (m, 2H), 1.52-1.47 (m, 2H), 1.32 (t, J=7.6 Hz, 2H). $^{13}$C NMR (100 MHz, $CDCl_3$) δ 162.0, 161.5, 157.8, 155.6, 154.1, 144.2, 135.0, 129.5, 127.8, 127.7, 106.4, 101.0, 98.2, 58.0, 55.6, 53.3, 52.5, 47.0, 46.0, 42.2, 29.7, 29.5, 26.2, 24.5. HRMS (ESI) calculated for $C_{24}H_{27}F_4N_7NaO^+$: 528.2105, found 528.2107.

Example 36: Preparation of Compound 36 compound 36

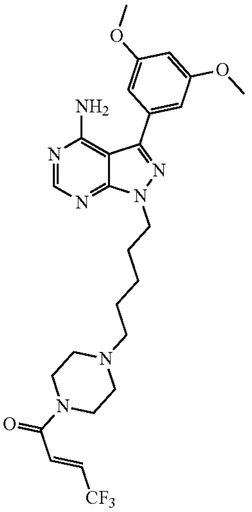

A specific preparation method was the same as the preparation method of compound 10, except that one of the raw materials was equimolar 4,4,4-trifluorocrotonic acid, in replacement of acryloyl chloride in the preparation method of compound (1-3). NMR test results of the compound 36 were as follows:

$^{1}$H NMR (400 MHz, $CDCl_3$) δ 8.32 (s, 1H), 6.92 (dt, J=15.4, 2.1 Hz, 1H), 6.78 (d, J=2.3 Hz, 2H), 6.73-6.64 (m, 1H), 6.52 (t, J=2.3 Hz, 1H), 4.40 (t, J=7.2 Hz, 2H), 3.82 (s, 6H), 3.65 (t, J=5.2 Hz, 2H), 3.50 (t, J=5.0 Hz, 2H), 2.40 (q, J=4.7 Hz, 4H), 2.32 (t, J=7.5 Hz, 2H), 1.96 (p, J=7.4 Hz, 2H), 1.52 (q, J=7.6 Hz, 2H), 1.36 (q, J=8.2 Hz, 2H). $^{13}$C NMR (100 MHz, $CDCl_3$) δ 162.3, 161.8, 158.1, 155.8, 154.3, 144.4, 135.3, 129.7, 129.4, 128.0, 127.9, 121.4, 106.6, 101.3, 98.5, 58.3, 55.8, 53.5, 52.7, 47.3, 46.2, 42.5, 29.9, 29.8, 26.4, 24.7. HRMS (ESI) calculated for $C_{26}H_{32}F_3N_7NaO_3^+$: 570.2411, found 570.2413.

Example 37: Preparation of Compound 37 compound 37

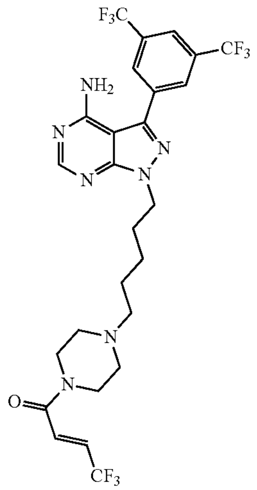

A specific preparation method was the same as the preparation method of compound 34, except that one of the raw materials was equimolar 4,4,4-trifluorobutenoic acid in replacement of acryloyl chloride in the preparation method of compound (1-3). NMR test results of the compound 37 were as follows:

$^1$H NMR (400 MHz, $CDCl_3$) δ 8.43 (d, J=2.3 Hz, 1H), 8.20 (s, 2H), 7.99 (s, 1H), 6.94 (d, J=15.5 Hz, 1H), 6.72 (dt, J=14.9, 6.8 Hz, 1H), 4.48 (t, J=7.0 Hz, 2H), 3.69 (s, 2H), 3.54 (s, 2H), 2.41 (d, J=31.2 Hz, 6H), 2.02 (q, J=7.8 Hz, 2H), 1.59 (s, 2H), 1.44-1.26 (m, 2H). $^{13}$C NMR (100 MHz, $CDCl_3$) δ 164.1, 162.1, 161.6, 157.4, 155.9, 154.7, 141.3, 136.6, 127.7, 121.0, 118.9, 118.7, 113.4, 113.2, 98.2, 58.0, 53.3, 52.5, 47.2, 45.9, 42.2, 29.7, 29.5, 26.1, 24.5, 14.1. HRMS (ESI) calculated for $C_{26}H_{26}F_9N_7NaO^+$: 646.1947, found 646.1947.

Example 38: Preparation of Compound 38 compound 38

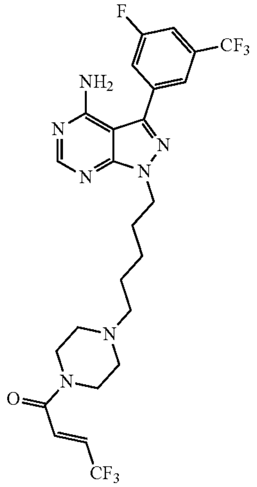

A specific preparation method was the same as the preparation method of compound 35, except that one of the raw materials was equimolar 4,4,4-trifluorobutenoic acid, in replacement of acryloyl chloride in the preparation method of compound (1-3). NMR test results of the compound 38 were as follows:

$^1$H NMR (400 MHz, $CDCl_3$) δ 8.43 (d, J=2.3 Hz, 1H), 8.20 (s, 2H), 7.99 (s, 1H), 6.94 (d, J=15.5 Hz, 1H), 6.71 (dq, J=14.2, 6.7 Hz, 1H), 4.48 (t, J=7.0 Hz, 2H), 3.69 (s, 2H), 3.54 (s, 2H), 2.41 (d, J=31.2 Hz, 6H), 2.01 (t, J=7.6 Hz, 2H), 1.59 (s, 2H), 1.48-1.27 (m, 2H). $^{13}$C NMR (100 MHz, $CDCl_3$) δ 162.0, 155.2, 154.6, 142.9, 133.2, 132.1, 132.1, 129.4, 129.0, 128.6, 128.5, 127.9, 121.3, 120.8, 111.6, 105.6, 58.1, 53.3, 52.6, 46.9, 46.0, 42.3, 29.5, 26.3, 24.5, 22.1. HRMS (ESI) calculated for $C_{26}H_{26}F_9N_7NaO^+$: 646.1947, found 646.1947.

Example 39: Preparation of Compound 39 compound 39

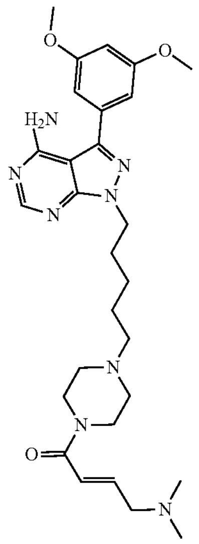

A specific preparation method was the same as the preparation method of compound 10, except that one of the raw materials was equimolar trans-4-dimethylaminocrotonic acid, in replacement of acryloyl chloride in the preparation method of compound (1-3). NMR test results of the compound 39 were as follows:

$^{1}$H NMR (400 MHz, $CDCl_3$) δ 8.38 (s, 1H), 6.81 (d, J=2.3 Hz, 2H), 6.56 (t, J=2.3 Hz, 1H), 5.60 (s, 2H), 4.43 (t, J=7.2 Hz, 2H), 3.86 (s, 6H), 3.67 (t, J=5.1 Hz, 2H), 3.59 (t, J=5.1 Hz, 2H), 3.49 (s, 1H), 2.45 (t, J=5.1 Hz, 4H), 2.33 (t, J=7.4 Hz, 2H), 1.96 (d, J=7.5 Hz, 2H), 1.50-1.35 (m, 4H). $^{13}$C NMR (100 MHz, $CDCl_3$) δ 161.5, 161.5, 157.7, 155.9, 144.0, 135.1, 106.4, 101.0, 100.0 98.3, 58.1, 55.6, 53.1, 52.4, 52.3, 49.4, 47.1, 45.8, 43.4, 43.3, 43.2, 37.4, 29.6, 26.9, 26.5. HRMS (ESI) calculated for $C_{25}H_{31}N_7NaO_3^+$: 500.2831, found 500.2833.

Example 40: Preparation of Compound 40 compound 40

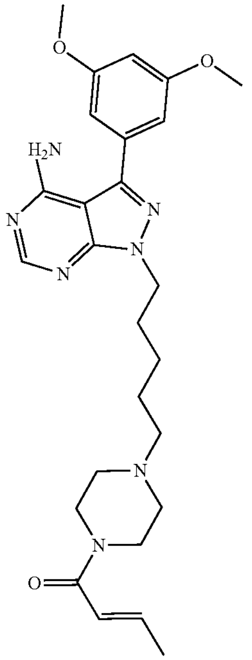

A specific preparation method was the same as the preparation method of compound 10, except that one of the raw materials was equimolar crotonic acid, in replacement of acryloyl chloride in the preparation method of compound (1-3). NMR test results of the compound 40 were as follows:

$^{1}$H NMR (400 MHz, $CDCl_3$) δ 8.31 (s, 1H), 6.88-6.73 (m, 3H), 6.52 (t, J=2.3 Hz, 1H), 6.20 (dq, J=15.0, 1.7 Hz, 1H), 4.39 (t, J=7.2 Hz, 2H), 3.82 (s, 6H), 3.62 (d, J=8.1 Hz, 2H), 3.56-3.43 (m, 2H), 2.36 (t, J=5.1 Hz, 4H), 2.29 (dd, J=8.7, 6.4 Hz, 2H), 2.01-1.91 (m, 2H), 1.83 (dd, J=6.9, 1.7 Hz, 3H), 1.52 (t, J=7.6 Hz, 2H), 1.36 (ddd, J=15.3, 9.1, 5.4 Hz, 2H). $^{13}$C NMR (100 MHz, $CDCl_3$) δ 165.5, 161.5, 158.0, 155.7, 154.1, 144.1, 141.5, 135.1, 121.4, 119.9, 106.4, 101.1, 98.2, 60.4, 58.2, 55.5, 53.5, 53.4, 52.8, 47.0, 45.5, 41.8, 29.6, 26.2, 24.5, 18.2. HRMS (ESI) calculated for $C_{26}H_{35}N_7NaO_3^+$: 516.2694, found 516.2696.

Example 41 Enzyme Activity Test

In the present disclosure, the homogeneous time-resolved fluorescence (HTRF) technology was used to evaluate an inhibitory effect of a compound on the four subtypes FGFR1, FGFR2, FGFR3, and FGFR4. FGFR1, FGFR2, FGFR3, and FGFR4 prokaryotic expression vectors were first constructed; and when the prokaryotic expression vectors were identified as correct, FGFR proteins were expressed and purified on a large scale in an *Escherichia coli* (*E. coli*) system, and protein concentrations were determined. Resulting proteins were stored in aliquots. Before an enzyme activity test was started, cisbio HTRF KinEA (62TK0PEB) was used to pre-dilute each component required in an enzyme activity system with an enzyme activity buffer to a required working concentration. A 384-well plate (66PL384025) was prepared, 5 μL of a protein solution, 1 μL of a compound, and 2 μL of a substrate were added to each well, and 2 μL of ATP was finally added to initiate a reaction. Three parallel experiments were set for each concentration. In the blank control group, 1 μL of the compound was replaced with 1 μL of dimethyl sulfoxide (DMSO); and in the positive control group, the positive drug AZD4547 was used instead, and the other conditions remained unchanged. The 384-well plate was sealed and incubated at room temperature for about 1 h. After the incubation was completed, 5 μL of a lanthanide-labeled phosphorylated substrate antibody (a donor) and 5 μL of a streptavidin-labeled XL665 (a receptor) were added to each well to stop the reaction, and the plate was further incubated at room temperature for about 1 h in the dark. Finally, the TECAN infinite M1000PRO multi-function microplate reader was used to detect a fluorescence signal, an inhibition rate was calculated, and an IC50 value was fitted with GraphPad Prism 7.0.

Results showed that the compounds 1 to 40 could inhibit the protein activity of FGFR1/2/3/4 to varying degrees.

TABLE 1
Structure-activity relationship (SAR) studies based on enzyme activity results
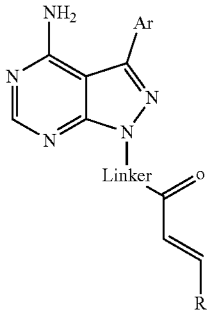
| Compound No. | Ar | Linker | R | Enzyme activity (IC50/nM) FGFR1 | FGFR2 | FGFR3 | FGFR4 |
| --- | --- | --- | --- | --- | --- | --- | --- |
| 1 | 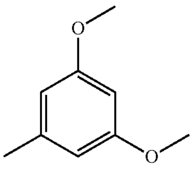 | 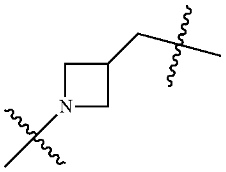 [SMILES: *CC1CN(*)C1] | H | 315 | 540 | 520 | 1921 |
| 2 | | 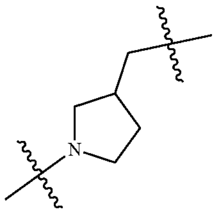 [SMILES: *CC1CCN(*)C1] | | 818 | 666 | 525 | >5000 |
| 3 | | 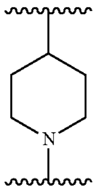 [SMILES: *C1CCN(*)CC1] | | 433 | 424 | 371 | 2730 |
| 4 | | 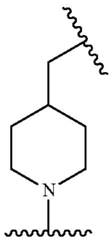 [SMILES: *CC1CCN(*)CC1] | | 615 | 641 | 521 | >5000 |
| 5 | | 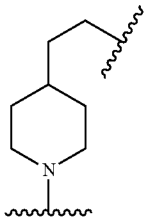 [SMILES: *CCC1CCN(*)CC1] | | 741 | 1210 | 580 | 1780 |

TABLE 1-continued
Structure-activity relationship (SAR) studies based on enzyme activity results
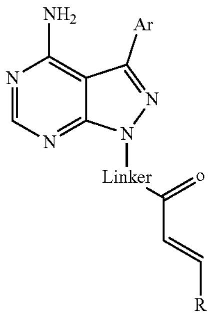
| Compound No. | Ar | Linker | R | Enzyme activity (IC50/nM) FGFR1 | FGFR2 | FGFR3 | FGFR4 |
|---|---|---|---|---|---|---|---|
| 6 | | 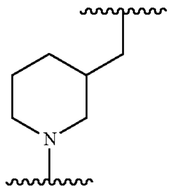 [SMILES: *CC1CCCN(*)C1] | | 790 | 1130 | 769 | >5000 |
| 7 | | 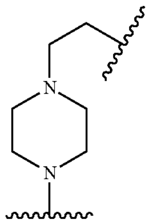 [SMILES: *CCN1CCN(*)CC1] | | 372 | 455 | 335 | 1610 |
| 8 | | 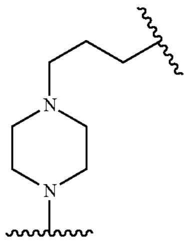 [SMILES: *CCCN1CCN(*)CC1] | | 323 | 351 | 414 | 40 |
| 9 | | 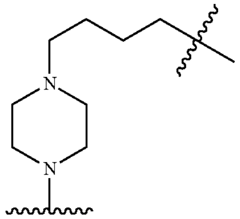 [SMILES: *CCCCN1CCN(*)CC1] | | 36.0 | 27.4 | 22.5 | 4210 |
| 10 | | 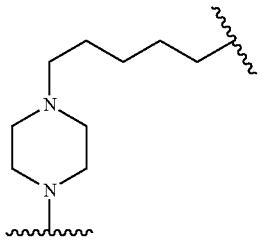 [SMILES: *CCCCCN1CCN(*)CC1] | | 3.2 | 1.4 | 2.7 | 3270 |

TABLE 1-continued
Structure-activity relationship (SAR) studies based on enzyme activity results
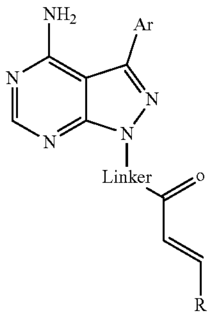
| Compound No. | Ar | Linker | R | Enzyme activity (IC50/nM) FGFR1 | FGFR2 | FGFR3 | FGFR4 |
|---|---|---|---|---|---|---|---|
| 11 | | 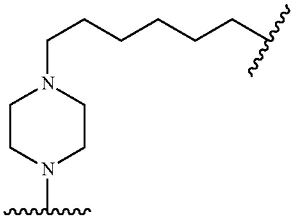 [SMILES: *CCCCCCN1CCN(*)CC1] | | 12.9 | 11.2 | 11.3 | 3207 |
| 12 | | 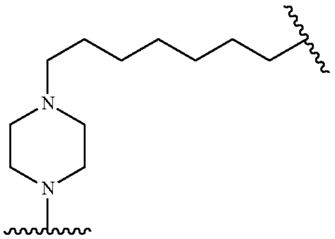 [SMILES: *CCCCCCCN1CCN(*)CC1] | | 5.9 | 2.2 | 3.4 | >5000 |
| 13 | 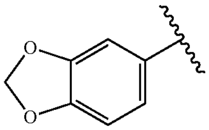 [SMILES: *c1ccc2c(c1)OCO2] | | | 476 | 78 | 875 | 2709 |
| 14 | 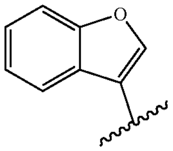 [SMILES: *c1coc2ccccc12] | | | 2109 | 1864 | 344 | >5000 |
| 15 | 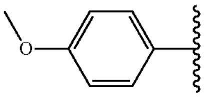 [SMILES: *c1ccc(OC)cc1] | | | >5000 | 3121 | >5000 | >5000 |
| 16 | 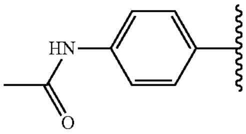 [SMILES: *c1ccc(NC(C)=O)cc1] | 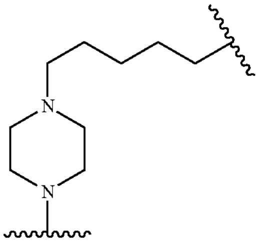 [SMILES: *CCCCCN1CCN(*)CC1] | | 1353 | 2511 | 1321 | >5000 |

TABLE 1-continued
Structure-activity relationship (SAR) studies based on enzyme activity results
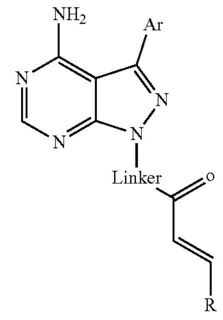
| Compound No. | Ar | Linker | R | Enzyme activity (IC50/nM) FGFR1 | FGFR2 | FGFR3 | FGFR4 |
|---|---|---|---|---|---|---|---|
| 17 | 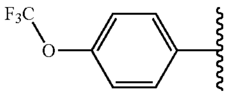 | | | 3523 | 4111 | >5000 | >5000 |
| 18 | 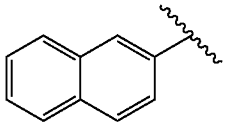 [SMILES: *c1ccc2ccccc2c1] | | | >5000 | >5000 | >5000 | >5000 |
| 19 | 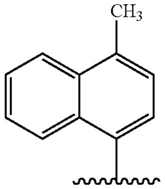 [SMILES: *c1ccc(C)c2ccccc12] | | | >5000 | >5000 | >5000 | >5000 |
| 20 | 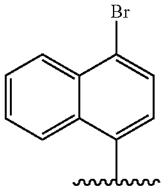 [SMILES: *c1ccc(Br)c2ccccc12] | | | >5000 | >5000 | >5000 | >5000 |
| 21 | 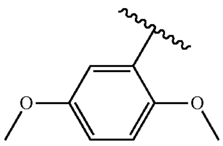 | | | 866 | 954 | 1978 | >5000 |
| 22 | 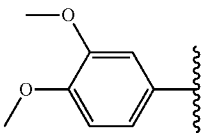 [SMILES: *c1ccc(OC)c(OC)c1] | | | 324 | 231 | 523 | >5000 |
| 23 | 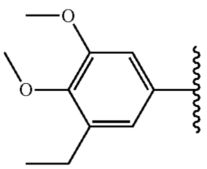 [SMILES: *c1cc(CC)c(OC)c(OC)c1] | | | 277 | 223 | 486 | 4910 |

TABLE 1-continued
Structure-activity relationship (SAR) studies based on enzyme activity results
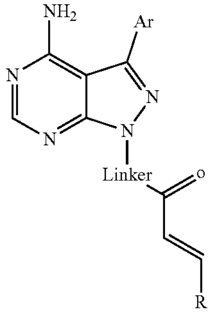
| Compound No. | Ar | Linker | R | Enzyme activity (IC50/nM) FGFR1 | FGFR2 | FGFR3 | FGFR4 |
|---|---|---|---|---|---|---|---|
| 24 | 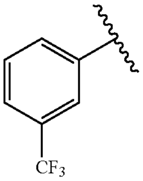 | | | 1877 | >5000 | >5000 | 3903 |
| 25 | 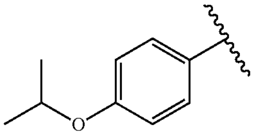 [SMILES: *c1ccc(OC(C)C)cc1] | | | >5000 | >5000 | >5000 | 2246 |
| 26 | 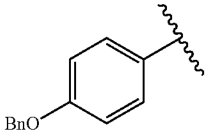 [SMILES: *c1ccc(OCc2ccccc2)cc1] | | | 1501 | 2345 | >5000 | >5000 |
| 27 | 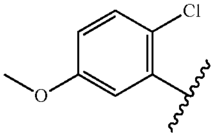 [SMILES: *c1cc(OC)ccc1Cl] | | | 554 | 763 | 731 | 2723 |
| 28 | 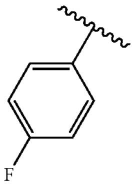 | | | 185 | 337 | 321 | 2987 |
| 29 | 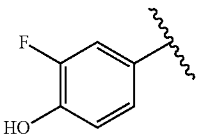 [SMILES: *c1ccc(O)c(F)c1] | | | 417 | 560 | 318 | 2580 |
| 30 | 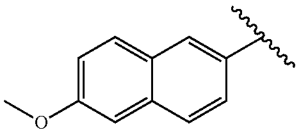 [SMILES: *c1ccc2cc(OC)ccc2c1] | | | >5000 | >5000 | >5000 | >5000 |

TABLE 1-continued
Structure-activity relationship (SAR) studies based on enzyme activity results
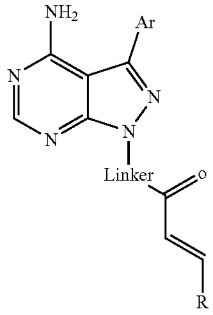
| Compound | | | | Enzyme activity (IC50/nM) | | | |
|---|---|---|---|---|---|---|---|
| No. | Ar | Linker | R | FGFR1 | FGFR2 | FGFR3 | FGFR4 |
| 31 | 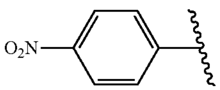 | | | >5000 | >5000 | >5000 | >5000 |
| 32 | 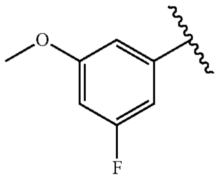 [SMILES: *c1cc(F)cc(OC)c1] | | | 118 | 133 | 132 | >5000 |
| 33 | 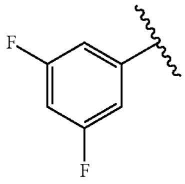 [SMILES: *c1cc(F)cc(F)c1] | | | 790 | >10 | >10 | 4112 |
| 34 | 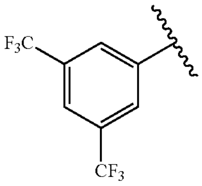 [SMILES: *c1cc(C(F)(F)F)cc(C(F)(F)F)c1] | | | 133 | 165 | 115 | 3921 |
| 35 | 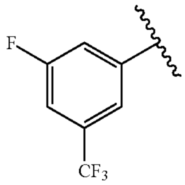 | | | 14.1 | 29.3 | 13.2 | 4102 |
| 36 | 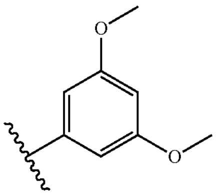 [SMILES: *c1cc(OC)cc(OC)c1] | | $CF_3$ | 0.7 | 0.7 | 0.9 | 809 |

TABLE 1-continued

Structure-activity relationship (SAR) studies based on enzyme activity results

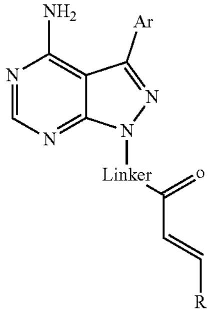

| Compound No. | Ar | Linker | R | Enzyme activity (IC50/nM) FGFR1 | FGFR2 | FGFR3 | FGFR4 |
|---|---|---|---|---|---|---|---|
| 37 | 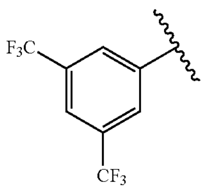 | | | 9.9 | 12.1 | 10.2 | >5000 |
| 38 | 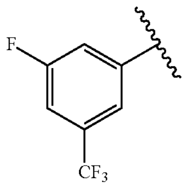 | | | 101 | 65 | 97 | 2401 |
| 39 | 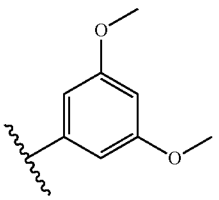 [SMILES: *c1cc(OC)cc(OC)c1] | | $(CH_3)_2NCH_2$ | 13.8 | 37.5 | 15.5 | >5000 |
| 40 | | | $CH_3$ | 16.6 | 26.3 | 12.4 | >5000 |
| AZD4547 | | NA | | 1.1 | 2.2 | 1.8 | 660 |

Example 42 Cell Proliferation Assay

In the present disclosure, the compounds 10 and 36 were selected, and the methyl thiazolyl tetrazolium (MTT) colorimetric method was used to evaluate the proliferation inhibition effects of the compounds 10 and 36 on various tumor cells. Tumor cells in a logarithmic growth phase were collected through trypsinization and resuspended in 1 mL of a fresh medium, and a small amount of a resulting suspension was taken, diluted, and subjected to cell counting with a hemocytometer. According to the cell growth rate, tumor cells were inoculated into a 96-well plate at a density of 3,000 cells/well to 5,000 cells/well, and then cultivated in an incubator for 24 h. The tumor cells were treated with the compounds 10 and 36 at 8 concentrations, with three replicate wells for each concentration, and then incubated for 96 h. After the incubation was completed, 10 μL of an MTT solution (5 mg/mL) was added to each well, and the plate was tapped for thorough mixing and then further incubated in an incubator for 3 h to 4 h. After the incubation was completed, the liquid in the well plate was carefully pipetted and removed, and then 100 μL of a DMSO solution was added to each well. Programs of a microplate reader were set to determine the absorbance values at 490 nm and 570 nm respectively, a proliferation inhibition rate at each concentration was calculated according to a formula, and the Graphpad Prism 7 software was finally used for data processing to calculate IC50.

The results (Table 1) showed that the compounds 10 and 36 significantly inhibited the proliferation of human squamous cell lung carcinoma cell NCI-H1581 (FGFR1 amplification) and human gastric cancer cell SNU-16 (FGFR2 amplification) and inhibited the proliferation of human hepatoma cell SK-hep-1 (FGFR4 amplification) to some degree, but exhibited no obvious inhibitory effect on tumor cells with normal FGFR expression, indicating that the compounds 10 and 36 had strong selectivity.

TABLE 2

| Anti-proliferation activities of the compound 36 for specific cancer cell lines | | | | | |
|---|---|---|---|---|---|
| | IC50/μM | | | | |
| Compound | NCI-H1581 FGFR1 amplification | SNU-16 FGFR2 amplification | SK-hep-1 FGFR4 amplification | Huh-7 | A549 |
| AZD4547 | 0.042 ± 0.002 | 0.006 ± 0.001 | 2.78 ± 0.069 | >10 | >10 |
| 10 | 0.051 ± 0.003 | 0.037 ± 0.005 | 2.86 ± 0.250 | >10 | >10 |
| 36 | 0.055 ± 0.008 | 0.043 ± 0.006 | 3.05 ± 0.120 | >10 | >10 |

Example 43 Inhibition of the Compounds 10 and 36 on FGF/FGFR and Downstream Signaling Pathways Thereof To further elucidate the influence of the compounds 10 and 36 on FGF/FGFR signaling, the influence of the compounds on FGFR and downstream signaling protein phosphorylation was verified by western blot (WB). Each of human squamous cell lung carcinoma cells NCI-H1581 and human gastric cancer cells SNU-16 in a logarithmic growth phase were collected through trypsinization and resuspended in 1 mL of a fresh medium, and a small volume of a resulting tumor cell suspension was taken, diluted, and subjected to cell counting with a hemocytometer. A corresponding volume of the tumor cell suspension was taken and inoculated into a 6-well plate at a density of $3\times10^5$ cells/well, and cultivated in an incubator for 24 h. After the cells were completely adherence, the used medium was pipetted and removed, fresh media with the compounds 10 and 36 at different concentrations were added, and the plate was incubated in an incubator for 12 h. After the incubation was completed, a culture supernatant was pipetted and removed, and the plate was washed three times with a pre-cooled 1×PBS solution to completely pipet and remove the residual solution; 60 μL of an RIPA lysis buffer was added to each well, and cells were gently scraped off with a cell scraper; a resulting lysis buffer was transferred to a 1.5 mL EP tube, subjected an ice bath for 10 min, and centrifuged at 14,000 rpm for 10 min, a resulting supernatant was pipetted into a new 1.5 mL EP tube, and a small amount of the supernatant was pipetted for protein content determination; and a corresponding volume of 5×loading buffer was added to the remaining supernatant, and a resulting mixture was vortexed for thorough mixing and subjected a metal bath at 100° C. for 10 min. According to a determined protein content, a corresponding loading amount was calculated at 30 μg of protein per well. Proteins were isolated by 8% sodium dodecyl sulfate-polyacrylamide gel electrophoresis (SDS-PAGE), the isolated proteins were transferred to a polyvinylidene fluoride (PVDF) membrane, and stained with Ponceau S, and the PDVF membrane with proteins was cut according to a molecular weight of a target protein, rinsed with a 1×TBST solution to remove Ponceau S, and blocked with 5% skimmed milk powder for 30 min. The PDVF membrane was washed three times with a 1× TBST solution, a PDVF membrane with the target protein band was placed in an incubation box, a corresponding primary antibody incubation solution was added, and the PDVF membrane was incubated at 4° C. overnight. After the primary antibody incubation was completed, the membrane was washed three times with a 1× TBST solution, a corresponding secondary antibody incubation solution was added, and the membrane was incubated at room temperature for 1.5 h. After the incubation was completed, the membrane was washed three times with a 1× TBST solution and subjected to color development with a hypersensitive horseradish peroxidase (HRP) chemiluminescence kit.

Figure 2:
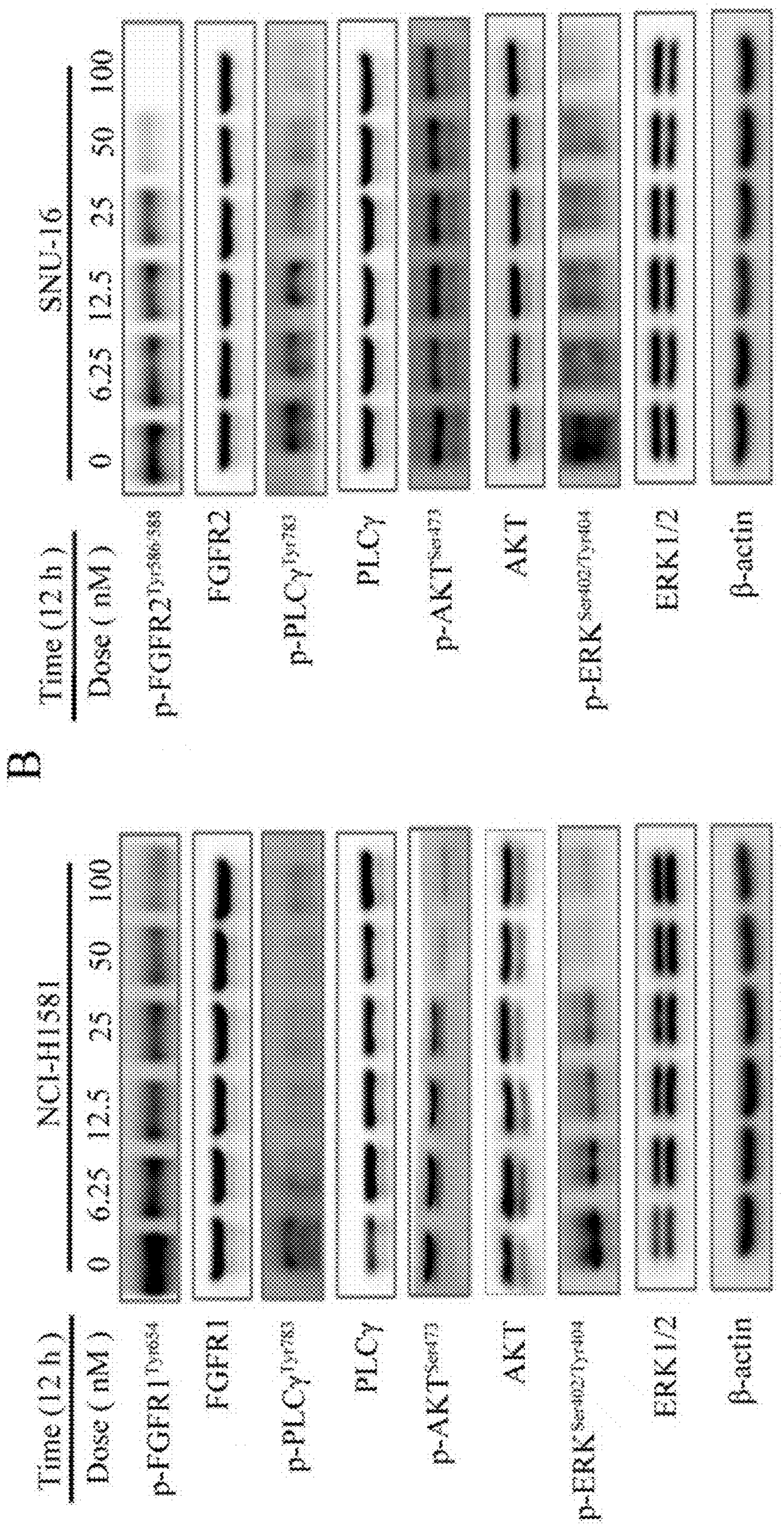
FIGS. 2A and 2B show that the compound 36 inhibits the activation of FGFR1 and a downstream signaling pathway thereof in NCI-H1581 cells and inhibits the activation of FGFR2 and a downstream signaling pathway thereof in SUN-16 cells in a concentration gradient-dependent manner, where

As shown in FIGS. 1A, 1B, 2A and 2B, the compounds 10 and 36 not only significantly inhibited the phosphorylation of FGFR1 in NCI-H1581 cells and the phosphorylation of FGFR2 in SNU-16 cells, but also inhibited the activation of downstream PLCγ, AKT, and ERK in a dose-dependent manner. In a word, the compounds 10 and 36 can strongly inhibit FGF/FGFR and downstream signaling pathways in vitro.

Example 44 Significant Inhibition of the Compounds 10 and 36 on Tumor Growth in Mice In order to evaluate an anti-tumor effect of the compounds 10 and 36 in vivo, a mouse subcutaneous xenograft model was established with human squamous cell lung carcinoma cells NCI-H1581 with high FGFR1 expression. Cells in a logarithmic growth phase were collected through trypsinization, washed three times with 1×PBS. A resulting cell precipitation was diluted to $1\times10^8$ cells/mL with a resuspending solution (1640 medium:Matrigel=1:1), and inoculated into inferior extremity of armpits of anterior limbs of 5-6 week-old female BALB/c Nude mice at $5\times10^6$ cells/mouse. When a tumor volume grew to 50 $mm^3$ to 100 $mm^3$, the mice were randomly divided into three groups (control group, 50 mg/kg, and 100 mg/kg), with 6 mice in each group. The compound 10 was administered orally every day, and the compound 36 was intraperitoneally injected every day. The tumor volume and mouse body weight were measured. The mice was treated after 26 d of administration, that a tumor tissue was dissected and fixed in a formalin solution for later use.

Figure 3:
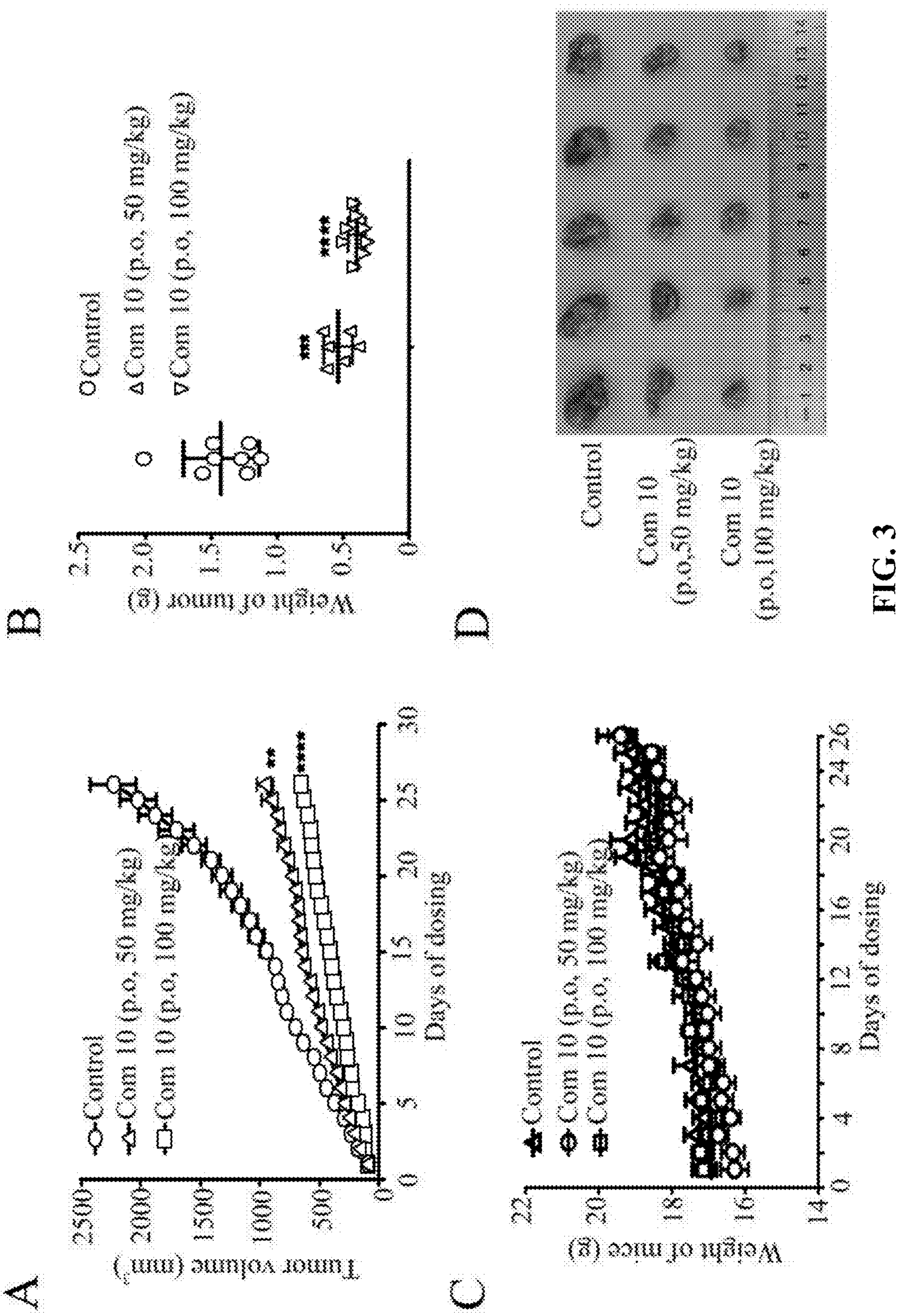
FIGS. 3A, 3B, 3C and 3D show tumor volume curves (FIG. 3A), a tumor weight statistics chart after 26 d of treatment (FIG. 3B), body weight change curves during a treatment process (FIG. 3C), and a picture of tumors after 26 d of treatment (FIG. 3D) in a tumor model subcutaneously transplanted with NCI-H1581 tumor cells under the tumor proliferation inhibition of the compound 10.
Figure 4:
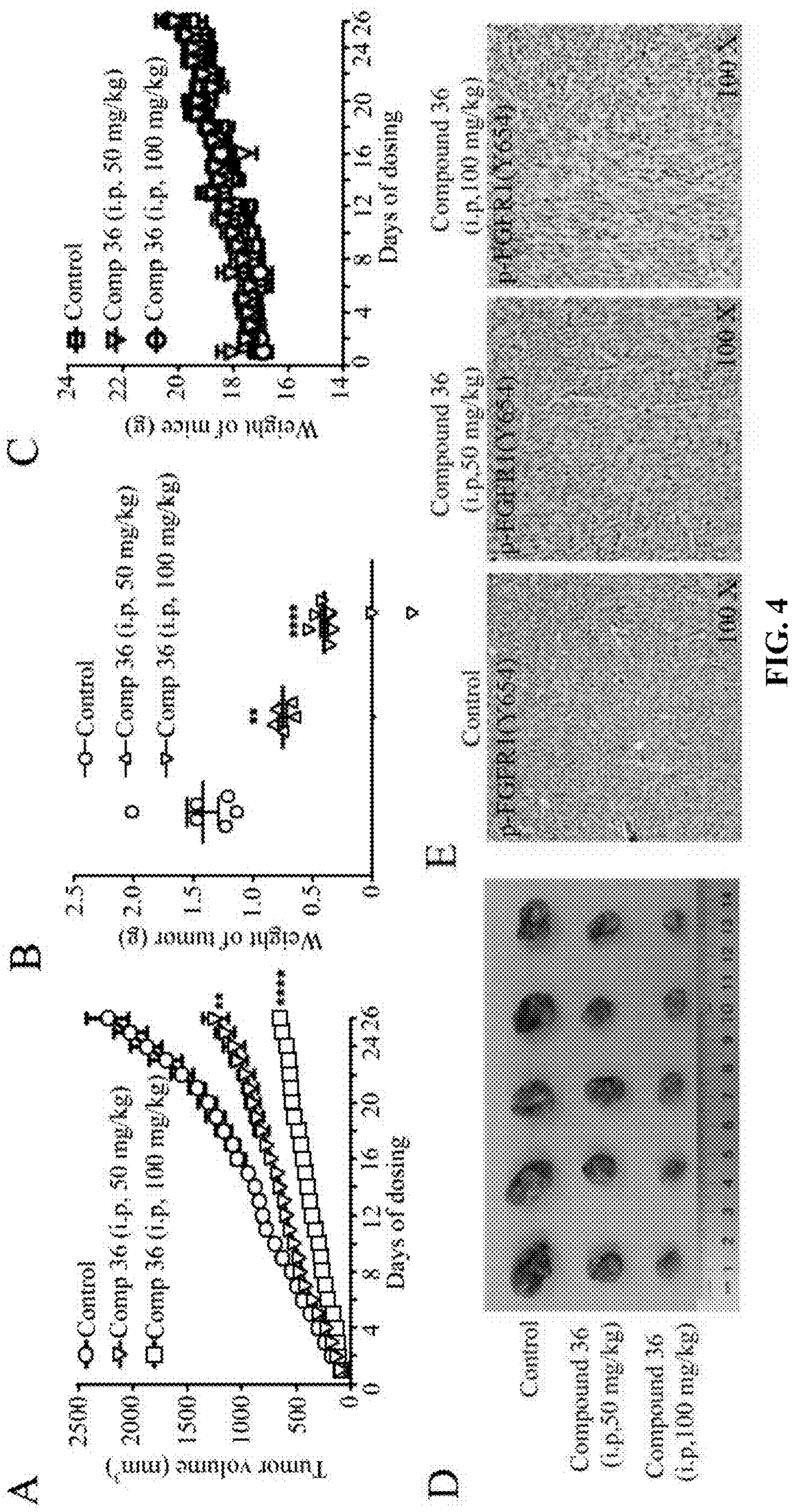
FIGS. 4A, 4B, 4C, 4D and 4E show tumor volume change curves (FIG. 4A), a tumor weight statistics chart after 26 d of treatment (FIG. 4B), body weight change curves during a treatment process (FIG. 4C), a picture of tumors after 26 d of treatment (FIG. 4D), and phosphorylation levels of FGFR1 in tissues of different treatments detected by immunohistochemistry (IHC) (FIG. 4E) in a tumor model subcutaneously transplanted with NCI-H1581 tumor cells under the tumor proliferation inhibition of the compound 36.

As shown in FIGS. 3A, 3B, 3C, 3D, 4A, 4B, 4C, 4D and 4E, the compounds 10 and 36 inhibited the proliferation of NCI-H1581 cells in mice in a dose-dependent manner, with an inhibition rate of 72% in the high-dose group; inhibited the phosphorylation activation of FGFR1 in a tumor tissue; and did not lead to an obvious weight loss, indicating that the compounds 10 and 36 were well tolerated in vivo at all doses.

In conclusion, the present disclosure optimizes 2H-pyrazolo[3,4-d]pyrimidine to obtain novel derivatives thereof (compounds 10 and 36), and the compounds 10 and 36 are served as effective and selective inhibitors for FGFR1, FGFR2, and FGFR3, which exhibit an irreversible binding effect to a target protein. The compounds are leading compounds that can not only inhibit FGF/FGFR and downstream signaling pathways thereof at low concentrations, but also exhibit significant anti-proliferation effects on the NCI-H1581 cancer cell line in vitro and in vivo. In addition, the compounds 10 and 36 show low toxicity and prominent PK properties, and are currently identified as potential drug candidates.

The above are merely examples of the present disclosure, and are not intended to limit the present disclosure. Any modification, equivalent substitution, and improvement fall within the spirit and principle of the present disclosure should be included in the claimed scope of the present disclosure.

REFERENCES (1) Turner, N.; Grose, R. Fibroblast growth factor signalling: from development to cancer. Nat. Rev. Cancer 2010, 10, 116-129.

(2) Carter, E. P.; Fearon, A. E.; Grose, R. P. Careless talk costs lives: fibroblast growth factor receptor signalling and the consequences of pathway malfunction. Trends Cell Biol. 2015, 25, 221-233.

(3) Touat, M.; Ileana, E.; Postel-Vinay, S.; Andre, F.; Soria, J. C. Targeting FGFR signaling in cancer. Clin. Cancer Res. 2015, 21, 2684-2694.

(4) Dieci, M. V; Arnedos, M.; Andre, F.; Soria, J. C. Fibroblast growth factor receptor inhibitors as a cancer treatment: from a biologic rationale to medical perspectives. Cancer Discovery 2013, 3, 264-279.

(5) Hagel, M.; Miduturu, C.; Sheets, M.; Rubin, N.; Weng, W.; Stransky, N.; Bifulco, N.; Kim, J. L.; Hodous, B.; Brooijmans, N.; Shutes, A.; Winter, C.; Lengauer, C.; Kohl, N. E.; Guzi, T. First selective small molecule inhibitor of FGFR4 for the treatment of hepatocellular carcinomas with an activated FGFR4 signaling pathway. Cancer Discovery 2015, 5, 424-437.

(6) Babina, I. S.; Turner, N. C. Advances and challenges in targeting FGFR signalling in cancer. Nat. Rev. Cancer 2017, 17, 318-332.

(7) Renhowe, P. A.; Pecchi, S.; Shafer, C. M.; Machajewski, T. D.; Jazan, E. M.; Taylor, C.; Antonios-McCrea, W.; McBride, C. M.; Frazier, K.; Wiesmann, M.; Lapointe, G. R.; Feucht, P. H.; Warne, R. L.; Heise, C. C.; Menezes, D.; Aardalen, K.; Ye, H.; He, M.; Le, V; Vora, J.; Jansen, J. M.; Wernette-Hammond, M. E.; Harris, A. L. Design, structure-activity relationships and in vivo characterization of 4-amino-3-benzimidazol-2-ylhydroquinolin-2-ones: a novel class of receptor tyrosine kinase inhibitors. J. Med. Chem. 2009, 52, 278-292.

(8) Bello, E.; Colella, G.; Scarlato, V; Oliva, P.; Berndt, A.; Valbusa, G.; Serra, S. C.; D'Incalci, M.; Cavalletti, E.; Giavazzi, R.; Damia, G.; Camboni, G. E-3810 is a potent dual inhibitor of VEGFR and FGFR that exerts antitumor activity in multiple preclinical models. Cancer Res. 2011, 71, 1396-1405.

(9) Roth, G. J.; Heckel, A.; Colbatzky, F.; Handschuh, S.; Kley, J.; Lehmann-Lintz, T.; Lotz, R.; Tontsch-Grunt, U.; Walter, R.; Hilberg, F. Design, synthesis, and evaluation of indolinones as triple angiokinase inhibitors and the discovery of a highly specific 6-methoxycarbonyl-substituted indolinone (BIBF 1120). J. Med. Chem. 2009, 52, 4466-4480.

(10) Gozgit, J. M.; Wong, M. J.; Moran, L.; Wardwell, S.; Mohemmad, Q. K.; Narasimhan, N. I.; Shakespeare, W. C.; Wang, F.; Clackson, T.; Rivera, V. M. Ponatinib (AP24534), a multitargeted pan-FGFR inhibitor with activity in multiple FGFR-amplified or mutated cancer models. Mol. Cancer Ther. 2012, 11, 690-699.

(11) Gavine, P. R.; Mooney, L.; Kilgour, E.; Thomas, A. P.; Al-Kadhimi, K.; Beck, S.; Rooney, C.; Coleman, T.; Baker, D.; Mellor, M. J.; Brooks, A. N.; Klinowska, T. AZD4547: an orally bioavailable, potent, and selective inhibitor of the fibroblast growth factor receptor tyrosine kinase family. Cancer Res. 2012, 72, 2045-2056.

(12) Guagnano, V; Furet, P.; Spanka, C.; Bordas, V.; Le Douget, M.; Stamm, C.; Brueggen, J.; Jensen, M. R.; Schnell, C.; Schmid, H.; Wartmann, M.; Berghausen, J.; Drueckes, P.; Zimmerlin, A.; Bussiere, D.; Murray, J.; Graus Porta, D. Graus Porta, D. Discovery of 3-(2,6-dichloro-3,5-dimethoxy-phenyl)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase. J. Med. Chem. 2011, 54, 7066-7083.

(13) Zhao, G.; Li, W. Y.; Chen, D.; Henry, J. R.; Li, H. Y.; Chen, Z.; Zia-Ebrahimi, M.; Bloem, L.; Zhai, Y.; Huss, K.; Peng, S. B.; McCann, D. J. A novel, selective inhibitor of fibroblast growth factor receptors that shows a potent broad spectrum of antitumor activity in several tumor xenograft models. Mol. Cancer Ther. 2011, 10, 2200-2210.

(14) Perera, T. P. S.; Jovcheva, E.; Mevellec, L.; Vialard, J.; De Lange, D.; Verhulst, T.; Paulussen, C.; Van De Ven, K.; King, P.; Freyne, E.; Rees, D. C.; Squires, M.; Saxty, G.; Page, M.; Murray, C. W.; Gilissen, R.; Ward, G.; Thompson, N. T.; Newell, D. R.; Cheng, N.; Xie, L.; Yang, J.; Platero, S. J.; Karkera, J. D.; Moy, C.; Angibaud, P.; Laquerre, S.; Lorenzi, M. V. Discovery and pharmacological characterization of JNJ-42756493 (erdafitinib), a functionally selective small-molecule FGFR family inhibitor. Mol. Cancer Ther. 2017, 16, 1010-1020.

(15) Zhou, W.; Hur, W.; McDermott, U.; Dutt, A.; Xian, W.; Ficarro, S. B.; Zhang, J.; Sharma, S. V; Brugge, J.; Meyerson, M.; Settleman, J.; Gray, N. S. A structure-guided approach to creating covalent FGFR inhibitors. Chem. Biol. 2010, 17, 285-295.

(16) Tan, L.; Wang, J.; Tanizaki, J.; Huang, Z.; Aref, A. R.; Rusan, M.; Zhu, S. J.; Zhang, Y; Ercan, D.; Liao, R. G.; Capelletti, M.; Zhou, W.; Hur, W.; Kim, N.; Sim, T.; Gaudet, S.; Barbie, D. A.; Yeh, J. R. J.; Yun, C. H.; Hammerman, P. S.; Mohammadi, M.; Janne, P. A.; Gray, N. S. Development of covalent inhibitors that can overcome resistance to first-generation FGFR kinase inhibitors. Proc. Natl. Acad. Sci. U.S.A. 2014, 111, E4869-E4877.

(17) Brown, W. S.; Tan, L.; Smith, A.; Gray, N. S.; Wendt, M. K. Covalent targeting of fibroblast growth factor receptor inhibits metastatic breast cancer. Mol. Cancer Ther. 2016, 15, 2096-2106.

(18) Brameld, K. A.; Owens, T. D.; Verner, E.; Venetsanakos, E.; Bradshaw, J. M.; Phan, V. T.; Tam, D.; Leung, K.; Shu, J.; LaStant, J.; Loughhead, D. G.; Ton, T.; Karr, D. E.; Gerritsen, M. E.; Goldstein, D. M.; Funk, J. O. Discovery of the irreversible covalent FGFR inhibitor 8-(3-(4-acryloylpiperazin-1-yl)propyl)-6-(2,6-di chloro-3,5-dimethoxyphenyl)-2-(methylamino)pyrido[2,3-d]pyrimidin-7(8H)-one (PRN1371) for the treatment of solid tumors. J. Med. Chem. 2017, 60, 6516-6527.

(19) Wang, Y; Dai, Y; Wu, X.; Li, F.; Liu, B.; Li, C.; Liu, Q.; Zhou, Y.; Wang, B.; Zhu, M.; Cui, R.; Tan, X.; Xiong, Z.; Liu, J.; Tan, M.; Xu, Y.; Geng, M.; Jiang, H.; Liu, H.; Ai, J.; Zheng, M. Discovery and Development of a Series of Pyrazolo[3,4-d]pyridazinone Compounds as the Novel Covalent Fibroblast Growth Factor Receptor Inhibitors by the Rational Drug Design. J. Med. Chem. 2019, 62, 7473-7488.

(20) Wang, Y; Li, L.; Fan, J.; Dai, Y.; Jiang, A.; Geng, M.; Ai, J.; Duan, W. Discovery of Potent Irreversible Pan-Fibroblast Growth Factor Receptor (FGFR) Inhibitors. J. Med. Chem. 2018, 61, 9085-9104.

(21) Li, X.; Guise, C. P.; Taghipouran, R.; Yosaatmadja, Y.; Ashoorzadeh, A.; Paik, W.; Squire, C. J.; Jiang, S.; Luo, J.; Xu, Y; Tu, Z.; Lu, X.; Ren, X.; Patterson, A. V; Smaill, J. B.; Ding, K. 2-Oxo-3,4-dihydropyrimido[4, 5-d]pyrimidinyl derivatives as new irreversible pan fibroblast growth factor receptor (FGFR) inhibitors. Eur. J. Med. Chem. 135, 2017, 531-543.

What is claimed is:

1. A compound of formula I or a pharmaceutically acceptable salt thereof:

formula I

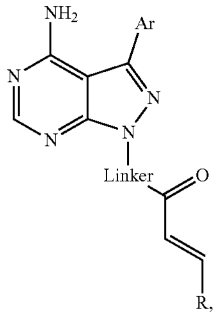

wherein in formula I, Ar is

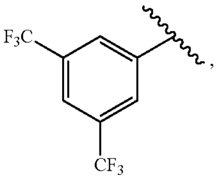,

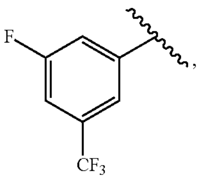, or

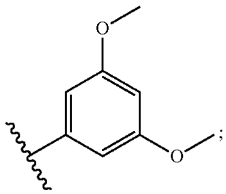;

R is H, $CF_3$, $(CH_3)_2NCH_2$, or $CH_3$; and

Linker is

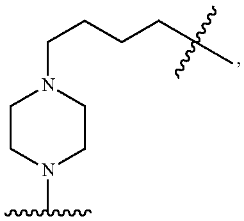,

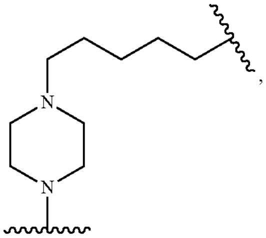,

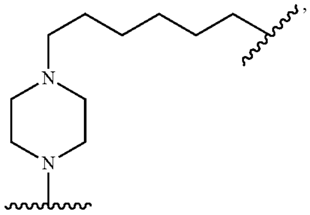, or

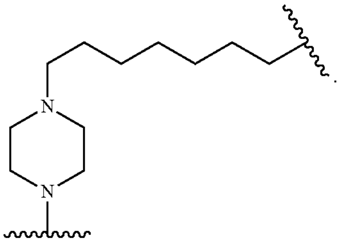.

2. The compound or the pharmaceutically acceptable salt thereof according to claim 1, wherein the compound is one selected from the group consisting of:

compound 9

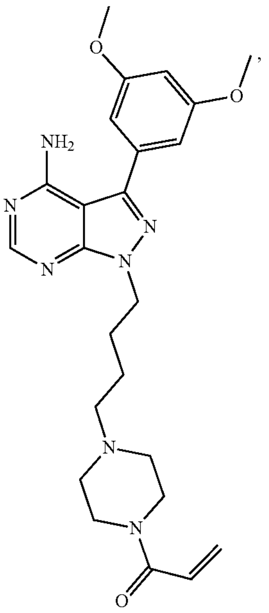,

-continued
compound 10
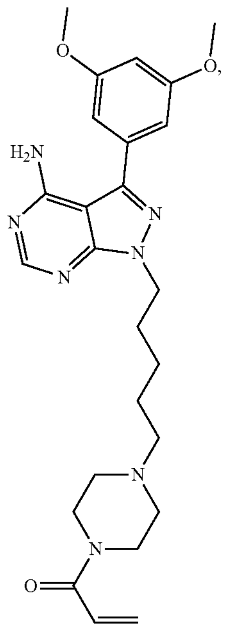
compound 12
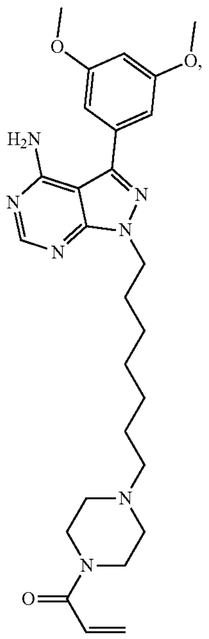
compound 11
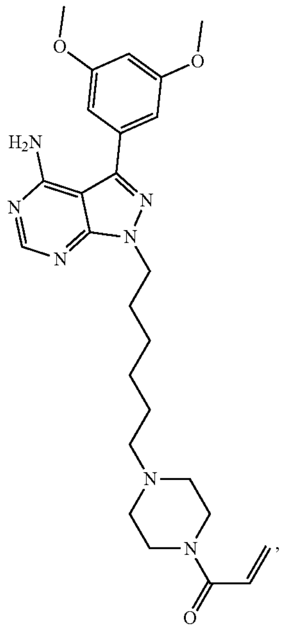
compound 35
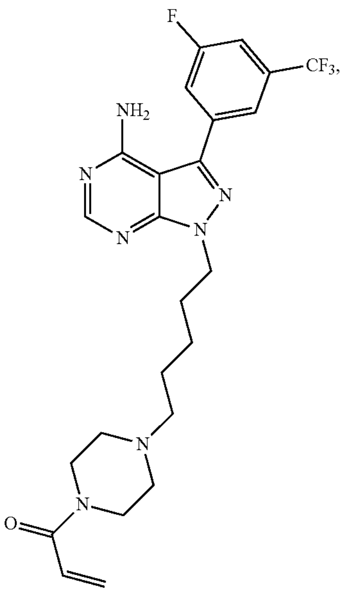

-continued
compound 36
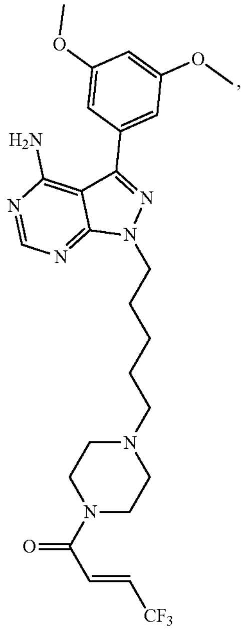
,
compound 37
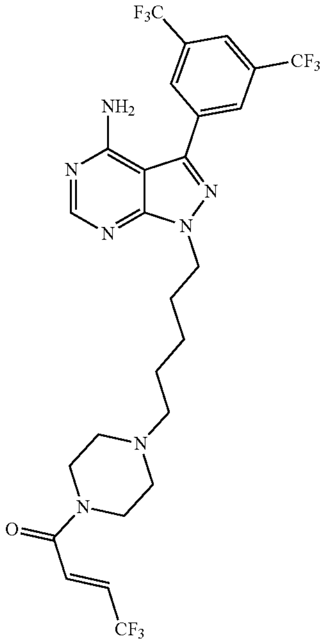
-continued
compound 39
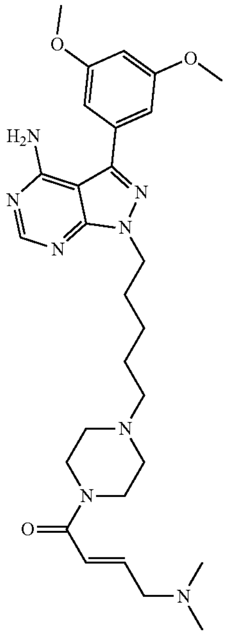
, and
compound 40
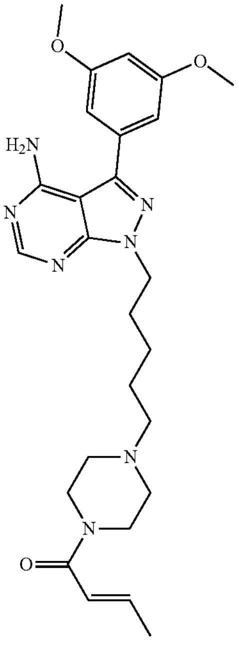
.
3. A method for preparing the compound or the pharmaceutically acceptable salt thereof according to claim 1, with a synthetic route as follows:
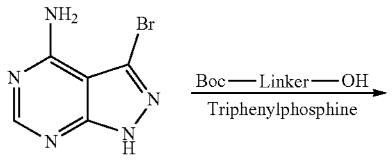

-continued

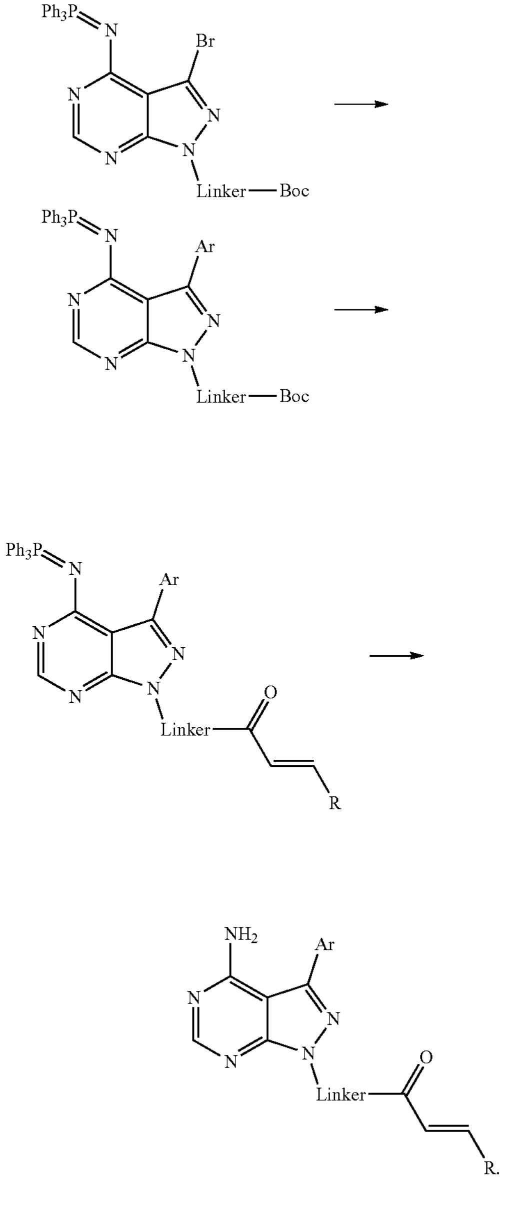

4. The method according to claim 3, comprising the following steps:

subjecting a compound with a structure shown in formula a and a compound with a structure shown in formula b to a Mitsunobu reaction in presence of triphenylphosphine at room temperature for 4 h to obtain a compound with a structure shown in formula c;

subjecting the compound with the structure shown in formula c and a compound with a structure shown in formula d to a Suzuki coupling reaction at 80° C. to obtain a compound with a structure shown in formula e;

subjecting the compound with the structure shown in formula e and trifluoroacetic acid (TFA) to a first deprotection reaction at 0° C., and then subjecting a resulting material to an acylation reaction at room temperature to obtain a compound with a structure shown in formula f; and subjecting the compound with the structure shown in formula f to a second deprotection reaction at room temperature to obtain the compound with a structure shown in formula I;

formula a

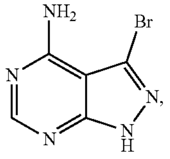

formula b

Boc—Linker—OH, formula c

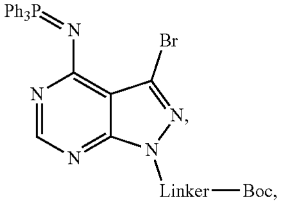

formula d

Ar—B(OH)$_2$, formula e

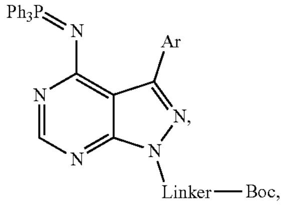

and formula f

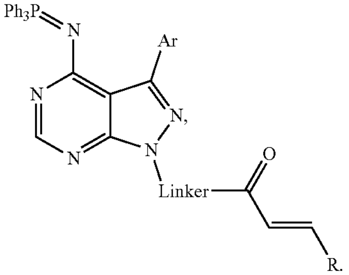

5. A method for treating a cancer, comprising the following step:

administering an anti-cancer drug to a patient through oral administration or intraperitoneal injection, wherein the anti-cancer drug comprises the compound or the pharmaceutically acceptable salt thereof according to claim 1 and wherein the cancer comprises at least one selected from the group consisting of non-small cell lung cancer, gastric cancer, and hepatoma.

6. The method according to claim 5, wherein the anti-cancer drug comprises compound 10 or compound 36, compound 10

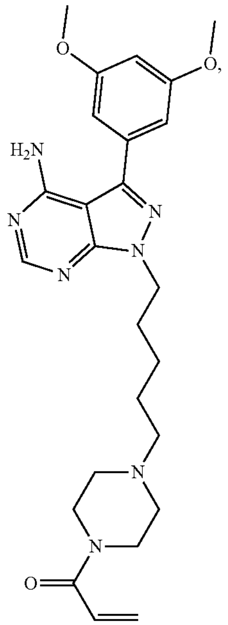

-continued compound 36

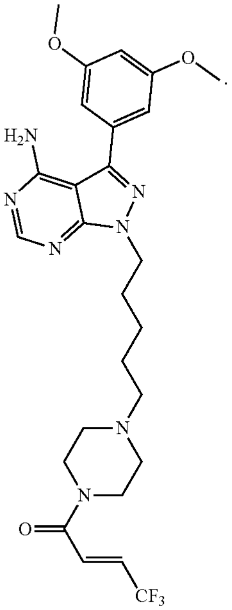

7. The method according to claim 6, wherein the anti-cancer drug is administered at a dose of 50 mg/kg or 100 mg/kg; and the dose of the anti-cancer drug is calculated according to an amount of the compound 10 or the compound 36.

8. The method according to claim 6, wherein when the anti-cancer drug comprises the compound 10, the anti-cancer drug is administered orally.

9. The method according to claim 6, wherein when the anti-cancer drug comprises the compound 36, the anti-cancer drug is administered through intraperitoneal injection.

* * * * *